US012703871B2

(12) United States Patent
Alarcon et al.

(10) Patent No.: US 12,703,871 B2
(45) Date of Patent: Aug. 11, 2026

(54) MAIZE EVENT DP-004114-3 AND METHODS FOR DETECTION THEREOF

(71) Applicants: PIONEER HI-BRED INTERNATIONAL, INC., Johnston, IA (US); E. I. DU PONT DE NEMOURS AND COMPANY, Wilmington, DE (US)

(72) Inventors: Clara Maria Alarcon, Altoona, IA (US); Matthew C. Harmon, Urbandale, IA (US); M. Alejandra Pascual, Granger, IA (US); James C. Register, III, Ames, IA (US); Christopher J. Scelonge, Ankeny, IA (US); Joshua K. Young, Johnston, IA (US); Cathy Xiaoyan Zhong, Wilmington, DE (US)

(73) Assignees: PIONEER HI-BRED INTERNATIONAL, INC., Johnston, IA (US); E. I. DU PONT DE NEMOURS AND COMPANY, Wilmington, DE (US)

( * ) Notice: Subject to any disclaimer, the term of this patent is extended or adjusted under 35 U.S.C. 154(b) by 354 days.

(21) Appl. No.: 18/159,396

(22) Filed: Jan. 25, 2023

(65) Prior Publication Data

US 2023/0220407 A1 Jul. 13, 2023

Related U.S. Application Data

(63) Continuation-in-part of application No. 16/997,530, filed on Aug. 19, 2020, now abandoned, which is a continuation of application No. 16/516,341, filed on Jul. 19, 2019, now abandoned, which is a continuation of application No. 15/648,112, filed on Jul. 12, 2017, now Pat. No. 10,407,688, which is a continuation of application No. 13/853,413, filed on Mar. 29, 2013, now Pat. No. 9,725,772.

(60) Provisional application No. 61/617,990, filed on Apr. 24, 2012.

(51) Int. Cl.
*C12N 15/82* (2006.01)
*C12Q 1/6895* (2018.01)

(52) U.S. Cl.
CPC ..... *C12N 15/8241* (2013.01); *C12N 15/8286* (2013.01); *C12Q 1/6895* (2013.01); *Y02A 40/146* (2018.01)

(58) Field of Classification Search
None
See application file for complete search history.

(56) References Cited

U.S. PATENT DOCUMENTS 6,222,106 B1 4/2001 Hall
7,129,042 B2 10/2006 Gillim-Ross et al.
7,294,773 B1 11/2007 Nyhus
7,342,153 B1 3/2008 Carlone
7,435,807 B1 10/2008 Barbour et al.
7,696,341 B2 * 4/2010 Bing .................... C12Q 1/6876 435/6.13
8,062,840 B2 * 11/2011 Anderson ............ C12Q 1/6895 536/22.1
8,575,434 B2 11/2013 Diehn et al.
9,725,772 B2 * 8/2017 Alarcon ............... C12Q 1/6895
9,790,156 B2 10/2017 White et al.
9,790,561 B2 10/2017 Diehn et al.
10,190,179 B2 1/2019 Diehn et al.
10,407,668 B2 9/2019 Agard et al.
10,407,688 B2 * 9/2019 Alarcon ............... C12Q 1/6895
11,155,883 B2 10/2021 Diehn et al.
2002/0182586 A1 12/2002 Morris et al.
2003/0033632 A1 2/2003 Crane et al.
2004/0181048 A1 9/2004 Wang
2006/0070139 A1 3/2006 Bing et al.
2007/0277258 A1 11/2007 Fisher et al.
2008/0176235 A1 7/2008 Bing et al.
2008/0178357 A1 7/2008 Bing et al.
2009/0094706 A1 4/2009 Binning et al.
2011/0154523 A1 6/2011 Diehn et al.
2015/0093747 A1 4/2015 Diehn et al.
2018/0023148 A1 1/2018 Diehn et al.
2019/0136331 A1 5/2019 Diehn et al.
2019/0338300 A1 11/2019 Alarcon et al.
2020/0385749 A1 12/2020 Alarcon et al.
2022/0002821 A1 1/2022 Diehn et al.

FOREIGN PATENT DOCUMENTS

CN 101641443 A 2/2010
EP 1620571 A2 2/2006
WO 9932642 A2 7/1999
WO 9964579 A2 12/1999
WO 0031268 A1 6/2000
WO 2004090143 A2 10/2004
WO 2004099447 A2 11/2004
WO 2005061720 A2 7/2005
WO 2005096804 A2 10/2005
WO 2007140256 A1 12/2007

(Continued)

OTHER PUBLICATIONS

Appenzeller, et al., "Subchronic feeding study with genetically modified stacked trait lepidopteran and coleopteran resistant (DAS-01507-1xDAS-59122-7) maize grain in Sprague-Dawley rats." Food and Chemical Toxicology, vol. 47: 1512-1520 (2009).

(Continued)

*Primary Examiner* — Medina A Ibrahim

(57) ABSTRACT

The invention provides DNA compositions that relate to transgenic insect resistant maize plants. Also provided are assays for detecting the presence of the maize DP-004114-3 event based on the DNA sequence of the recombinant construct inserted into the maize genome and the DNA sequences flanking the insertion site. Kits and conditions useful in conducting the assays are provided.

1 Claim, 5 Drawing Sheets

Specification includes a Sequence Listing.

(56) References Cited

FOREIGN PATENT DOCUMENTS

| | | | |
|---|---|---|---|
| WO | 2007142840 | A2 | 12/2007 |
| WO | 2008070845 | A2 | 6/2008 |
| WO | 2008/080166 | | 7/2008 |
| WO | 2008085729 | A2 | 7/2008 |
| WO | 2009/088732 | | 7/2009 |
| WO | 2009/100188 | | 8/2009 |
| WO | 2011/075595 | | 6/2011 |
| WO | 2011/084621 | A1 | 7/2011 |

OTHER PUBLICATIONS

Bravo, et al., "How to cope with insect resistance to Bt toxins?" Trends in Biotechnology, vol. 26: 573-579 (2008).
Castle, et al., "Agricultural input traits: past, present and future." Current Opinion in Biotechnology, vol. 17:105-112 (2006).
Chambers, et al., "Isolation and Characterization of a Novel Insecticidal Crystal Protein Gene from *Bacillus thuringiensis* subsp. *aizawai*." Journal of Bacteriology, vol. 173(13): 3966-3976 (1991).
Craig, et al., "An overview of general features of risk assessments of genetically modified crops." Euphytica, vol. 164: 853-880 (2008).
GenBank Accession No. AC211214. *Zea mays* chromosome 1 clone CH201-11 E23. Published Sep. 13, 2014. pp. 1.
GenBank Accession No. CP015774. Lelliottia amnigena strain ZB04. Published May 26, 2016. pp. 1.
GenBank Accession No. CP016352. Vibrio natriegens strain CCUG 16374 chromosome 2. Published Jul. 6, 2016. pp. 1.
GenBank Accession No. CP016182. *Escherichia coli* strain EC590. Published Jul. 8, 2016. pp 1.
Herman, et al., "Compositional assessment of event DAS-59122-7 maize using substantial equivalence." Regulatory Toxicology and Pharmacology, vol. 47: 37-47 (2007).
Liu, et al.: "An accurate and rapid PCR-based zygosity testing method for genetically modified maize." GMO Biosafety Research, 2010, vol. 1, No. 1, pp. 1-4.
Moellenbeck, et al., "Insecticidal proteins from Bacillus thuringiensis protect corn from corn rootworms." Nature Biotechnology, vol. 19: 668-672 (2001).
Storer, et al., "Field Measures of Western Corn Rootworm (Coleoptera: Chrysomelidae) Mortality Caused by Cry34/35Ab1 Proteins Expressed in Maize Event 59122 and Implications for Trait Durability." J. Econ. Entomology, vol. 99(4):1381-1387 (2006).
Wu, et al., "Susceptibility of Cry1Ab-resistant and -susceptible sugarcane borer (Lepidoptera: Crambidae) to four Bacillus thuringiensis toxins." Journal of Invertebrate Pathology, vol. 100: 29-34 (2009).
International Search Report and Written Opinion for International Application No. PCT/US2010/060818 completed on Mar. 11, 2011.
International Search Report and Written Opinion for International Application No. PCT/US2013/034374 completed on Jun. 20, 2013.
Zhang J., et al., "Integration of C4-Specific PPDK Gene of Maize to C3 Rice and Its Characteristics in Relation to Photosynthesis," Frontiers of Agriculture in China, vol. 1, No. 3, pp. 243-249.
Hua G., et aL., "Binding Analyses of Bacillus Thuringiensis Cry Delta-Endotoxins Using Brush Border Membrane Vesicles of Ostrinia Nubilalis," Applied and Environmental Microbiology, Feb. 2001, vol. 67, No. 2, pp. 872-879.
International Preliminary Report on Patentability for International Application No. PCT/US2010/060818, mailed Jun. 28, 2012, 7 Pages.
International Preliminary Report on Patentability for International Application No. PCT/US2013/034374, mailed Oct. 9, 2014, 5 Pages.
Kaiser-Alexnat R., et al., "Studies on the Proteolytic Processing and Binding of Bt Toxins Cry3Bb1 and Cry34Ab1/Cry35Ab1 in the Midgut of Western Corn Rootworm (*Diabrotica virgifera virgifera leconte*)," Insect Pathogens and Insect Parasitic Nematodes, 2009, vol. 45, pp. 235-238.
Lowe T., et al., "A Computer Program for Selection of Oligonucleotide Primers for Polymerase Chain Reactions," Nucleic Acid Research, 1990, vol. 18, No. 7, pp. 1757-1761.
Nucleic Acid Sequences Search Reports, AC No. ARP28594 and GC659853, 3 Pages.
Anonymous., "Decision document DD 2013-98: Determination of the safety of Pioneer Hi-Bred Production Ltd., (Limited)'s Corn (Zea Mays L. (Linnaeus)) event 4144," Issued on Jun. 2013, Retrieved on [Mar. 10, 2026], Retrieved from Internet URL: https://inspection.canada.ca/en/plant-varieties/plants-novel-traits/approved-under-review/decision-documents/dd-2013-98, 38 Pages.
Defendants' Second Supplemental Invalidity Contentions, *Corteva Agriscience LLC et al.*v. *Inari Agriculture, Inc. et al.*, C.A. No. 23-1059 (JFM) (D. Del. Sep. 8, 2025).
EFSA Panel on Genetically Modified Organism (GMO)., "Assessment of genetically modified maize 4114 for food and feed uses, under Regulation (EC) No 1829/2003 (application EFSA-GMO-NL-2014-123)," EFSA Journal European Food Safety Authority, 2018, vol. 16, No. 5, e05280, 25 Pages.
Pioneer Hi-Bred International, Inc., "Petition (11-244- 01p) for Determination of Nonregulated Status of Insect-Resistant and Herbicide-Tolerant Pioneer 4114 Maize: Event DP-004114-3," Final Enviromental Assessment, May 2013, 230 Pages.
Pu X., et al., "Adenlate Kinase [Shigella Flexneri 1a]," GenBank Acession No. ASQ83138, Aug. 2, 2017, 2 Pages.

* cited by examiner

MAIZE EVENT DP-004114-3 AND METHODS FOR DETECTION THEREOF

CROSS REFERENCE

This utility application is a continuation application of U.S. patent application Ser. No. 16/997,530, filed Aug. 19, 2020, which is a continuation of U.S. patent application Ser. No. 16/516,341, filed Jul. 19, 2019, which is a continuation of U.S. patent application Ser. No. 15/648,112, filed Jul. 12, 2017, now U.S. Pat. No. 10,407,688, which is a continuation of U.S. patent application Ser. No. 13/853,413, filed Mar. 29, 2013, now U.S. Pat. No. 9,725,772, which claims the benefit of U.S. Provisional Application No. 61/617,990 filed Apr. 24, 2012, the disclosures of each of which are incorporated herein by reference in their entireties.

REFERENCE TO SEQUENCE LISTING SUBMITTED ELECTRONICALLY

An XML formatted sequence listing having the file name "5251_SequenceListing.xml" created on Jan. 25, 2023, and having a size of 75,586 bytes is filed in computer readable form concurrently with the specification. The sequence listing contained in this XML formatted document is part of the specification and is herein incorporated by reference in its entirety.

FIELD OF INVENTION

Embodiments of the present invention relate to the field of plant molecular biology, specifically embodiment of the invention relate to DNA constructs for conferring insect resistance to a plant. Embodiments of the invention more specifically relate to insect resistant corn plant event DP-004114-3 and to assays for detecting the presence of corn event DP-004114-3 in a sample and compositions thereof.

BACKGROUND OF INVENTION

An embodiment of this invention relates to the insect resistant corn (*Zea mays*) plant DP-004114-3, also referred to as "maize line DP-004114-3," "maize event DP-004114-3," and "4114 maize," and to the DNA plant expression construct of corn plant DP-004114-3 and the detection of the transgene/flanking insertion region in corn plant DP-004114-3 and progeny thereof.

Corn is an important crop and is a primary food source in many areas of the world. Damage caused by insect pests is a major factor in the loss of the world's corn crops, despite the use of protective measures such as chemical pesticides. In view of this, insect resistance has been genetically engineered into crops such as corn in order to control insect damage and to reduce the need for traditional chemical pesticides. One group of genes which have been utilized for the production of transgenic insect resistant crops is the delta-endotoxin group from *Bacillus thuringiensis* (Bt). Delta-endotoxins have been successfully expressed in crop plants such as cotton, potatoes, rice, sunflower, as well as corn, and have proven to provide excellent control over insect pests. (Perlak, F. J et al. (1990) *Bio/Technology* 8:939-943; Perlak, F. J. et al. (1993) *Plant Mol. Biol.* 22:313-321; Fujimoto, H. et al. (1993) *Bio/Technology* 11:1151-1155; Tu et al. (2000) *Nature Biotechnology* 18:1101-1104; PCT publication WO 01/13731; and Bing, J. W. et al. (2000) Efficacy of Cry1F Transgenic Maize, $14^{th}$ Biennial International Plant Resistance to Insects Workshop, Fort Collins, CO).

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al. (1988) *Ann. Rev. Genet.* 22:421-477). At the same time the presence of the transgene at different locations in the genome will influence the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgene by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in U.S. Pat. No. 6,395,485 for the detection of elite event GAT-ZM1. Accordingly, it would be desirable to have a simple and discriminative method for the identification of event DP-004114-3.

SUMMARY OF INVENTION

Embodiments of this invention relate to methods for producing and selecting an insect resistant monocot crop plant. More specifically, a DNA construct is provided that when expressed in plant cells and plants confers resistance to insects. According to one aspect of the invention, a DNA construct, capable of introduction into and replication in a host cell, is provided that when expressed in plant cells and plants confers insect resistance to the plant cells and plants. Maize event DP-004114-3 was produced by *Agrobacterium*-mediated transformation with plasmid PHP27118. This event contains the cry1F, cry34Ab1, cry35Ab1, and pat gene cassettes, which confer resistance to certain lepidopteran and coleopteran pests, as well as tolerance to phosphinothricin.

Specifically, the first cassette contains a truncated version of the cry1F gene from *Bacillus thuringiensis* var. aizawai. The insertion of the cry1F gene confers resistance to damage by lepidopteran pests. The Cry1F protein (SEQ ID NO: 1) is comprised of 605 amino acids and has a molecular weight of approximately 68 kDa. The expression of the cry1F gene is controlled by the maize polyubiquitin promoter (Christensen et al. (1992) *Plant Mol. Biol.* 118(4):675-89), providing constitutive expression of the Cry1F protein in maize. This region also includes the 5' untranslated region (UTR) and intron associated with the native polyubiquitin promoter. The terminator for the cry1F gene is the poly(A) addition signal from Open Reading Frame 25 (ORF 25) of the *Agrobacterium tumefaciens* Ti plasmid pTi15955 (Barker et al. (1983) *Plant Mol. Biol.* 2:335-350).

The second cassette contains the cry34Ab1 gene isolated from *Bacillus thuringiensis* strain PS149B1 (U.S. Pat. Nos. 6,127,180; 6,624,145 and 6,340,593). The Cry34Ab1 protein (SEQ ID NO: 2) is 123 amino acid residues in length and has a molecular weight of approximately 14 kDa. The expression of the cry34Ab1 gene is controlled by a second copy of the maize polyubiquitin promoter with 5' UTR and intron (Christensen et al., 1992, supra). The terminator for the cry34Ab1 gene is the pinII terminator (Keil et al. (1986) *Nucleic Acids Res.* 14:5641-5650; An et al. (1989) *Plant Cell* 1:115-22).

The third gene cassette contains the cry35Ab1 gene, also isolated from *Bacillus thuringiensis* strain PS149B1 (U.S. Pat. Nos. 6,083,499; 6,548,291 and 6,340,593). The Cry35Ab1 protein (SEQ ID NO: 3) has a length of 383 amino acids and a molecular weight of approximately 44 kDa. Simultaneous expression of the Cry34Ab1 and Cry35Ab1 proteins in the plant confers resistance to coleopteran insects. The expression of the cry35Ab1 gene is controlled by the *Triticum aestivum* (wheat) peroxidase promoter and leader sequence (Hertig et al. (1991) *Plant Mol. Biol.* 16:171-174). The terminator for the cry35Ab1 gene is a second copy of the pinII terminator (Keil et al., 1986, supra; An et al., 1989, supra).

The fourth and final gene cassette contains a version of the phosphinothricin acetyl transferase gene from *Streptomyces viridochromogenes* (pat) that has been optimized for expression in maize. The pat gene expresses the phosphinothricin acetyl transferase enzyme (PAT) that confers tolerance to phosphinothricin. The PAT protein (SEQ ID NO: 4) is 183 amino acids residues in length and has a molecular weight of approximately 21 kDa. Expression of the pat gene is controlled by the promoter and terminator regions from the CaMV 35S transcript (Franck et al. (1980) *Cell* 21:285-294; Odell et al. (1985) *Nature* 313:810-812; Pietrzak, et al. (1986) *Nucleic Acids Res.* 14(14):5857-5868). Plants containing the DNA constructs are also provided.

According to another embodiment of the invention, compositions and methods are provided for identifying a novel corn plant designated DP-004114-3. The methods are based on primers or probes which specifically recognize the 5' and/or 3' flanking sequence of DP-004114-3. DNA molecules are provided that comprise primer sequences that when utilized in a PCR reaction will produce amplicons unique to the transgenic event DP-004114-3. The corn plant and seed comprising these molecules is an embodiment of this invention. Further, kits utilizing these primer sequences for the identification of the DP-004114-3 event are provided.

An additional embodiment of the invention relates to the specific flanking sequence of DP-004114-3 described herein, which can be used to develop specific identification methods for DP-004114-3 in biological samples. More particularly, the invention relates to the 5' and/or 3' flanking regions of DP-004114-3 which can be used for the development of specific primers and probes. A further embodiment of the invention relates to identification methods for the presence of DP-004114-3 in biological samples based on the use of such specific primers or probes.

According to another embodiment of the invention, methods of detecting the presence of DNA corresponding to the corn event DP-004114-3 in a sample are provided. Such methods comprise: (a) contacting the sample comprising DNA with a DNA primer set, that when used in a nucleic acid amplification reaction with genomic DNA extracted from corn event DP-004114-3 produces an amplicon that is diagnostic for corn event DP-004114-3; (b) performing a nucleic acid amplification reaction, thereby producing the amplicon; and (c) detecting the amplicon.

According to another embodiment of the invention, methods of detecting the presence of a DNA molecule corresponding to the DP-004114-3 event in a sample, such methods comprising: (a) contacting the sample comprising DNA extracted from a corn plant with a DNA probe molecule that hybridizes under stringent hybridization conditions with DNA extracted from corn event DP-004114-3 and does not hybridize under the stringent hybridization conditions with a control corn plant DNA; (b) subjecting the sample and probe to stringent hybridization conditions; and (c) detecting hybridization of the probe to the DNA. More specifically, a method for detecting the presence of a DNA molecule corresponding to the DP-004114-3 event in a sample, such methods, consisting of (a) contacting the sample comprising DNA extracted from a corn plant with a DNA probe molecule that consists of sequences that are unique to the event, e.g. junction sequences, wherein said DNA probe molecule hybridizes under stringent hybridization conditions with DNA extracted from corn event DP-004114-3 and does not hybridize under the stringent hybridization conditions with a control corn plant DNA; (b) subjecting the sample and probe to stringent hybridization conditions; and (c) detecting hybridization of the probe to the DNA.

In addition, a kit and methods for identifying event DP-004114-3 in a biological sample which detects a DP-004114-3 specific region are provided.

DNA molecules are provided that comprise at least one junction sequence of DP-004114-3; wherein a junction sequence spans the junction between heterologous DNA inserted into the genome and the DNA from the corn cell flanking the insertion site, i.e. flanking DNA, and is diagnostic for the DP-004114-3 event.

According to another embodiment of the invention, methods of producing an insect resistant corn plant that comprise the steps of: (a) sexually crossing a first parental corn line comprising the expression cassettes of the invention, which confers resistance to insects, and a second parental corn line that lacks insect resistance, thereby producing a plurality of progeny plants; and (b) selecting a progeny plant that is insect resistant. Such methods may optionally comprise the further step of back-crossing the progeny plant to the second parental corn line to producing a true-breeding corn plant that is insect resistant.

A further embodiment of the invention provides a method of producing a corn plant that is resistant to insects comprising transforming a corn cell with the DNA construct PHP27118, growing the transformed corn cell into a corn plant, selecting the corn plant that shows resistance to insects, and further growing the corn plant into a fertile corn plant. The fertile corn plant can be self pollinated or crossed with compatible corn varieties to produce insect resistant progeny.

Another embodiment of the invention further relates to a DNA detection kit for identifying maize event DP-004114-3 in biological samples. The kit comprises a first primer which specifically recognizes the 5' or 3' flanking region of DP-004114-3, and a second primer which specifically recognizes a sequence within the foreign DNA of DP-004114-3, or within the flanking DNA, for use in a PCR identification protocol. A further embodiment of the invention relates to a kit for identifying event DP-004114-3 in biological samples, which kit comprises a specific probe having a sequence which corresponds or is complementary to, a sequence having between 80% and 100% sequence identity with a specific region of event DP-004114-3. The sequence of the probe corresponds to a specific region comprising part of the 5' or 3' flanking region of event DP-004114-3.

The methods and kits encompassed by the embodiments of the present invention can be used for different purposes such as, but not limited to the following: to identify event DP-004114-3 in plants, plant material or in products such as, but not limited to, food or feed products (fresh or processed) comprising, or derived from plant material; additionally or alternatively, the methods and kits can be used to identify transgenic plant material for purposes of segregation between transgenic and non-transgenic material; additionally or alternatively, the methods and kits can be used to determine the quality of plant material comprising maize event DP-004114-3. The kits may also contain the reagents and materials necessary for the performance of the detection method.

A further embodiment of this invention relates to the DP-004114-3 corn plant or its parts, including, but not limited to, pollen, ovules, vegetative cells, the nuclei of pollen cells, and the nuclei of egg cells of the corn plant DP-004114-3 and the progeny derived thereof. The corn plant and seed of DP-004114-3 from which the DNA primer molecules provide a specific amplicon product is an embodiment of the invention.

The foregoing and other aspects of the invention will become more apparent from the following detailed description and accompanying drawing.

DETAILED DESCRIPTION

Figure 1:
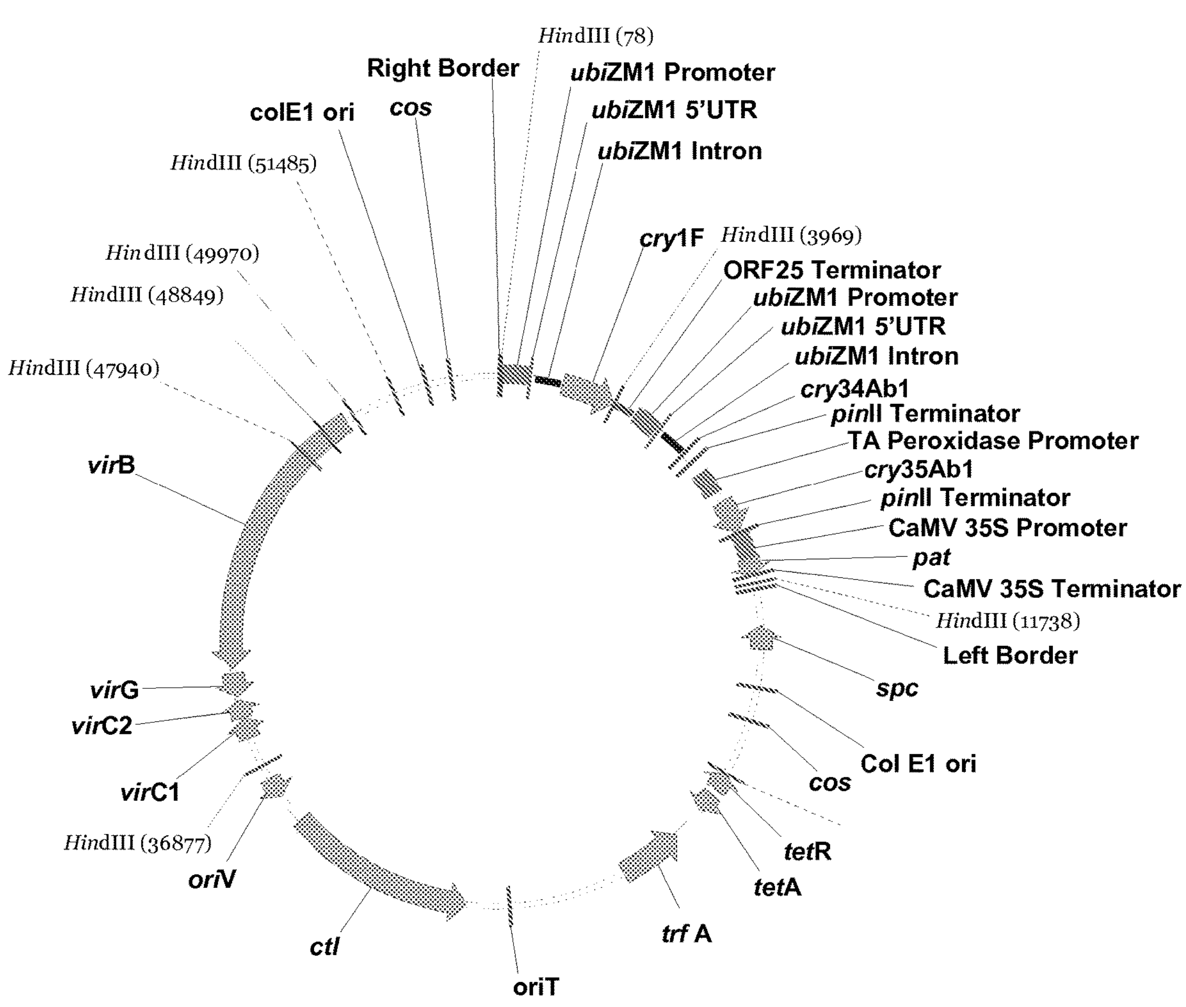
FIG. 1. Schematic diagram of plasmid PHP27118 with genetic elements indicated and Hind III restriction enzyme sites. Plasmid size is 54910 bp.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular,* $5^{th}$ edition, Springer-Verlag; New York, 1991; and Lewin, Genes V, Oxford University Press: New York, 1994. The nomenclature for DNA bases as set forth at 37 CFR § 1.822 is used.

The following table sets forth abbreviations used throughout this document, and in particular in the Examples section.

Table of Abbreviations

| | |
|---|---|
| 4114 maize | Maize containing event DP-004114-3 |
| bp | Base pair |
| *Bt* | *Bacillus thuringiensis* |
| CaMV | Cauliflower mosaic virus |
| cry1F | cty1F gene from *Bacillus thuringiensis* var. *aizawai* |
| Cry1F | Protein from cry1F gene |
| cry34Ab1 | cry34Ab1 gene from *Bacillus thuringiensis* strain PS149B1 |
| Cry34Ab1 | Protein from cry34Ab1 |
| cry35Ab1 | cry35Ab1 gene from *Bacillus thuringiensis* strain PS149B1 |
| Cry35Ab1 | Protein from cry35Ab1 gene |
| kb | Kilobase pair |
| kDa | KiloDalton |
| LB | Left T-DNA border |
| pat | phosphinothricin acetyl transferase gene |
| PAT | Protein from phosphinothricin acetyl transferase gene |
| PCR | Polymerase chain reaction |
| pinII | Proteinase inhibitor II gene from *Solanum tuberosum* |
| RB | Right T-DNA border |
| T-DNA | The transfer DNA portion of the *Agrobacterium* transformation plasmid between the Left and Right Borders that is expected to be transferred to the plant genome |
| UTR | Untranslated region |
| ECB | European corn borer (*Ostrinia nubilalis*) |
| FAW | Fall armyworm (*Spodoptera frugiperda*) |
| WCRW | western corn rootworm (*Diabrotica virgifera virgifera*) |

Compositions of this disclosure include seed deposited as Patent Deposit No. PTA-11506 and plants, plant cells, and seed derived therefrom. Applicant(s) have made a deposit of at least 2500 seeds of maize event DP-004114-3 with the American Type Culture Collection (ATCC), Manassas, VA 20110-2209 USA, on Nov. 24, 2010 and the deposits were assigned ATCC Deposit No. PTA-11506. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112. The seeds deposited with the ATCC on Nov. 24, 2010 were taken from the deposit maintained by Pioneer Hi-Bred International, Inc., 7250 NW 62$^{nd}$ Avenue, Johnston, Iowa 50131-1000. Access to this deposit will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. § 1.808, sample(s) of the deposit of at least 2500 seeds of hybrid maize with the American Type Culture Collection (ATCC), 10801 University Boulevard, Manassas, VA 20110-2209. This deposit of seed of maize event DP-004114-3 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant(s) have satisfied all the requirements of 37 C.F.R. §§ 1.801-1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or rights applicable to event DP-004114-3 under the Plant Variety Protection Act (7 USC 2321 et seq.). Unauthorized seed multiplication prohibited. The seed may be regulated.

As used herein, the term “comprising” means “including but not limited to.”

As used herein, the term “corn” means *Zea mays* or maize and includes all plant varieties that can be bred with corn, including wild maize species.

As used herein, the term “DP-004114-3 specific” refers to a nucleotide sequence which is suitable for discriminatively identifying event DP-004114-3 in plants, plant material, or in products such as, but not limited to, food or feed products (fresh or processed) comprising, or derived from plant material.

As used herein, the terms “insect resistant” and “impacting insect pests” refers to effecting changes in insect feeding, growth, and/or behavior at any stage of development, including but not limited to: killing the insect; retarding growth; preventing reproductive capability; inhibiting feeding; and the like.

As used herein, the terms “pesticidal activity” and “insecticidal activity” are used synonymously to refer to activity of an organism or a substance (such as, for example, a protein) that can be measured by numerous parameters including, but not limited to, pest mortality, pest weight loss, pest attraction, pest repellency, and other behavioral and physical changes of a pest after feeding on and/or exposure to the organism or substance for an appropriate length of time. For example “pesticidal proteins” are proteins that display pesticidal activity by themselves or in combination with other proteins.

“Coding sequence” refers to a nucleotide sequence that codes for a specific amino acid sequence. As used herein, the terms “encoding” or “encoded” when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

“Gene” refers to a nucleic acid fragment that expresses a specific protein, including regulatory sequences preceding (5' non-coding sequences) and following (3' non-coding sequences) the coding sequence. “Native gene” refers to a gene as found in nature with its own regulatory sequences. “Chimeric gene” refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. “Endogenous gene” refers to a native gene in its natural location in the genome of an organism. “Foreign” refers to material not normally found in the location of interest. Thus “foreign DNA” may comprise both recombinant DNA as well as newly introduced, rearranged DNA of the plant. A “foreign” gene refers to a gene not normally found in the host organism, but that is introduced into the host organism by gene transfer. Foreign genes can comprise native genes inserted into a non-native organism, or chimeric genes. A “transgene” is a gene that has been introduced into the genome by a transformation procedure. The site in the plant genome where a recombinant DNA has been inserted may be referred to as the “insertion site” or “target site”.

As used herein, “insert DNA” refers to the heterologous DNA within the expression cassettes used to transform the plant material while “flanking DNA” can exist of either genomic DNA naturally present in an organism such as a plant, or foreign (heterologous) DNA introduced via the transformation process which is extraneous to the original insert DNA molecule, e.g. fragments associated with the transformation event. A “flanking region” or “flanking sequence” as used herein refers to a sequence of at least 20 bp, preferably at least 50 bp, and up to 5000 bp, which is located either immediately upstream of and contiguous with or immediately downstream of and contiguous with the original foreign insert DNA molecule. Transformation procedures leading to random integration of the foreign DNA will result in transformants containing different flanking regions characteristic and unique for each transformant. When recombinant DNA is introduced into a plant through traditional crossing, its flanking regions will generally not be changed. Transformants will also contain unique junctions between a piece of heterologous insert DNA and genomic DNA, or two (2) pieces of genomic DNA, or two (2) pieces of heterologous DNA. A “junction” is a point where two (2) specific DNA fragments join. For example, a junction exists where insert DNA joins flanking DNA. A junction point also exists in a transformed organism where two (2) DNA fragments join together in a manner that is modified from that found in the native organism. “Junction DNA” refers to DNA that comprises a junction point. Two junction sequences set forth in this disclosure are the junction point between the maize genomic DNA and the 5' end of the insert as set forth in SEQ ID NO: 27, and the junction point between the 3' end of the insert and maize genomic DNA as set forth in SEQ ID NO: 28.

As used herein, “heterologous” in reference to a nucleic acid is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

A "protein" or "polypeptide" is a chain of amino acids arranged in a specific order determined by the coding sequence in a polynucleotide encoding the polypeptide.

A DNA construct is an assembly of DNA molecules linked together that provide one or more expression cassettes. The DNA construct may be a plasmid that is enabled for self replication in a bacterial cell and contains various endonuclease enzyme restriction sites that are useful for introducing DNA molecules that provide functional genetic elements, i.e., promoters, introns, leaders, coding sequences, 3' termination regions, among others; or a DNA construct may be a linear assembly of DNA molecules, such as an expression cassette. The expression cassette contained within a DNA construct comprises the necessary genetic elements to provide transcription of a messenger RNA. The expression cassette can be designed to express in prokaryote cells or eukaryotic cells. Expression cassettes of the embodiments of the present invention are designed to express in plant cells.

The DNA molecules of embodiments of the invention are provided in expression cassettes for expression in an organism of interest. The cassette will include 5' and 3' regulatory sequences operably linked to a coding sequence. "Operably linked" means that the nucleic acid sequences being linked are contiguous and, where necessary to join two protein coding regions, contiguous and in the same reading frame. Operably linked is intended to indicate a functional linkage between a promoter and a second sequence, wherein the promoter sequence initiates and mediates transcription of the DNA sequence corresponding to the second sequence. The cassette may additionally contain at least one additional gene to be co-transformed into the organism. Alternatively, the additional gene(s) can be provided on multiple expression cassettes or multiple DNA constructs.

The expression cassette will include in the 5' to 3' direction of transcription: a transcriptional and translational initiation region, a coding region, and a transcriptional and translational termination region functional in the organism serving as a host. The transcriptional initiation region (i.e., the promoter) may be native or analogous, or foreign or heterologous to the host organism. Additionally, the promoter may be the natural sequence or alternatively a synthetic sequence. The expression cassettes may additionally contain 5' leader sequences in the expression cassette construct. Such leader sequences can act to enhance translation.

It is to be understood that as used herein the term "transgenic" includes any cell, cell line, callus, tissue, plant part, or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

An insect resistant DP-004114-3 corn plant can be bred by first sexually crossing a first parental corn plant consisting of a corn plant grown from the transgenic DP-004114-3 corn plant and progeny thereof derived from transformation with the expression cassettes of the embodiments of the present invention that confers insect resistance, and a second parental corn plant that lacks insect resistance, thereby producing a plurality of first progeny plants; and then selecting a first progeny plant that is resistant to insects; and selfing the first progeny plant, thereby producing a plurality of second progeny plants; and then selecting from the second progeny plants an insect resistant plant. These steps can further include the back-crossing of the first insect resistant progeny plant or the second insect resistant progeny plant to the second parental corn plant or a third parental corn plant, thereby producing a corn plant that is resistant to insects.

As used herein, the term "plant" includes reference to whole plants, plant organs (e.g., leaves, stems, roots, etc.), seeds, plant cells, and progeny of same. Parts of transgenic plants understood to be within the scope of the invention comprise, for example, plant cells, protoplasts, tissues, callus, embryos as well as flowers, stems, fruits, leaves, and roots originating in transgenic plants or their progeny previously transformed with a DNA molecule of the invention and therefore consisting at least in part of transgenic cells, are also an embodiment of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference). Additional transformation methods are disclosed below.

Thus, isolated polynucleotides of the invention can be incorporated into recombinant constructs, typically DNA constructs, which are capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., (1985; Supp. 1987) *Cloning Vectors: A Laboratory Manual*, Weissbach and Weissbach (1989) *Methods for Plant Molecular Biology*, (Academic Press, New York); and Flevin et al., (1990) *Plant Molecular Biology Manual*, (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcos J. ed., American Society of Agronomy, Madison Wis. (1987).

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of isolated DNA from corn event DP-004114-3 whether from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the invention refer to their use for amplification of a target nucleic acid sequence, e.g., by PCR or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence specifically in the hybridization conditions or reaction conditions determined by the operator. This length may be of any length that is of sufficient length to be useful in a detection method of choice. Generally, 11 nucleotides or more in length, 18 nucleotides or more, and 22 nucleotides or more, are used. Such probes and primers hybridize specifically to a target sequence under high stringency hybridization conditions. Probes and primers according to embodiments of the present invention may have complete DNA sequence similarity of contiguous nucleotides with the target sequence, although probes differing from the target DNA sequence and that retain the ability to hybridize to target DNA sequences may be designed by conventional methods. Probes can be used as primers, but are generally designed to bind to the target DNA or RNA and are not used in an amplification process.

Specific primers can be used to amplify an integration fragment to produce an amplicon that can be used as a "specific probe" for identifying event DP-004114-3 in biological samples. When the probe is hybridized with the nucleic acids of a biological sample under conditions which allow for the binding of the probe to the sample, this binding can be detected and thus allow for an indication of the presence of event DP-004114-3 in the biological sample. Such identification of a bound probe has been described in the art. In an embodiment of the invention the specific probe is a sequence which, under optimized conditions, hybridizes specifically to a region within the 5' or 3' flanking region of the event and also comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of the event.

Methods for preparing and using probes and primers are described, for example, in Sambrook et al., *Molecular Cloning: A Laboratory Manual,* $2^{nd}$ ed., vol. 1-3, Cold Spring Harbor Laboratory Press, Cold Spring Harbor, N.Y. 1989 (hereinafter, "Sambrook et al., 1989"); Ausubel et al. eds., *Current Protocols in Molecular Biology*, Greene Publishing and Wiley-Interscience, New York, 1995 (with periodic updates) (hereinafter, "Ausubel et al., 1995"); and Innis et al., *PCR Protocols: A Guide to Methods and Applications*, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, WI); and Primer (Version 0.5©, 1991, Whitehead Institute for Biomedical Research, Cambridge, Mass.). Additionally, the sequence can be visually scanned and primers manually identified using guidelines known to one of skill in the art.

A "kit" as used herein refers to a set of reagents for the purpose of performing the method embodiments of the invention, more particularly, the identification of event DP-004114-3 in biological samples. The kit of the invention can be used, and its components can be specifically adjusted, for purposes of quality control (e.g. purity of seed lots), detection of event DP-004114-3 in plant material, or material comprising or derived from plant material, such as but not limited to food or feed products. "Plant material" as used herein refers to material which is obtained or derived from a plant.

Primers and probes based on the flanking DNA and insert sequences disclosed herein can be used to confirm (and, if necessary, to correct) the disclosed sequences by conventional methods, e.g., by re-cloning and sequencing such sequences. The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, a Practical Approach*, IRL Press, Washington, D.C. (1985), departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

In hybridization reactions, specificity is typically the function of post-hybridization washes, the critical factors being the ionic strength and temperature of the final wash solution. The thermal melting point ($T_m$) is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) and Sambrook et al. (1989).

As used herein, a substantially homologous sequence is a nucleic acid molecule that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in Ausubel et al. (1995), 6.3.1-6.3.6. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of a destabilizing agent such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1×SSC at 60 to 65° C. A nucleic acid of the invention may specifically hybridize to one or more of the nucleic acid molecules unique to the DP-004114-3 event or complements thereof or fragments of either under moderately stringent conditions.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, California); the ALIGN program (Version 2.0); the ALIGN PLUS program (version 3.0, copyright 1997); and GAP, BESTFIT, BLAST, FASTA, and TFASTA in the Wisconsin Genetics Software Package, Version 10 (available from Accelrys, 9685 Scranton Road, San Diego, CA 92121, USA). Alignments using these programs can be performed using the default parameters.

The CLUSTAL program is well described by Higgins and Sharp, *Gene* 73:237-244 (1988); Higgins and Sharp, *CABIOS* 5: 151-153 (1989); Corpet, et al., *Nucleic Acids Research* 16: 10881-90 (1988); Huang, et al., *Computer Applications in the Biosciences* 8: 155-65 (1992), and Pearson, et al., *Methods in Molecular Biology* 24: 307-331 (1994). The ALIGN and the ALIGN PLUS programs are based on the algorithm of Myers and Miller (1988) supra. The BLAST programs of Altschul et al. (1990) *J. Mol. Biol.* 215:403 are based on the algorithm of Karlin and Altschul (1990) supra. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Ausubel, et al., (1995). Alignment may also be performed manually by visual inspection.

To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether a corn plant resulting from a sexual cross contains transgenic event genomic DNA from the corn plant of the invention, DNA extracted from the corn plant tissue sample may be subjected to a nucleic acid amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the event DNA. Alternatively, the second primer may be derived from the flanking sequence. The amplicon is of a length and has a sequence that is also diagnostic for the event. The amplicon may range in length from the combined length of the primer pairs plus one nucleotide base pair to any length of amplicon producible by a DNA amplification protocol. Alternatively, primer pairs can be derived from flanking sequence on both sides of the inserted DNA so as to produce an amplicon that includes the entire insert nucleotide sequence of the PHP27118 expression construct as well as the sequence flanking the transgenic insert. A member of a primer pair derived from the flanking sequence may be located a distance from the inserted DNA sequence, this distance can range from one nucleotide base pair up to the limits of the amplification reaction, or about 20,000 bp. The use of the term "amplicon" specifically excludes primer dimers that may be formed in the DNA thermal amplification reaction.

Nucleic acid amplification can be accomplished by any of the various nucleic acid amplification methods known in the art, including PCR. A variety of amplification methods are known in the art and are described, inter alia, in U.S. Pat. Nos. 4,683,195 and 4,683,202 and in Innis et al., (1990) supra. PCR amplification methods have been developed to amplify up to 22 Kb of genomic DNA and up to 42 Kb of bacteriophage DNA (Cheng et al., *Proc. Natl. Acad. Sci. USA* 91:5695-5699, 1994). These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplicon produced by these methods may be detected by a plurality of techniques, including, but not limited to, Genetic Bit Analysis (Nikiforov, et al. *Nucleic Acid Res.* 22:4167-4175, 1994) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the pyrosequencing technique as described by Winge (2000) *Innov. Pharma. Tech.* 00:18-24. In this method an oligonucleotide is designed that overlaps the adjacent DNA and insert DNA junction. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence polarization as described by Chen et al., (1999) *Genome Res.* 9:492-498 is also a method that can be used to detect an amplicon of the invention. Using this method an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular beacons have been described for use in sequence detection as described in Tyangi et al. (1996) *Nature Biotech.* 14:303-308. Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

Maize event DP-004114-3 is effective against insect pests including insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Insects of the order Lepidoptera include, but are not limited to, armyworms, cutworms, loopers, and heliothines in the family Noctuidae: *Agrotis ipsilon* Hufnagel (black cutworm); *A. orthogonia* Morrison (western cutworm); A. segetum Denis & Schiffermüller (turnip moth); *A. subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira* (Xylomyges) *curialis* Grote (citrus cutworm); *Euxoa messoria* Harris (darksided cutworm); *Helicoverpa armigera* Hübner (American bollworm); *H. zea* Boddie (corn earworm or cotton bollworm); *Heliothis virescens* Fabricius (tobacco budworm); *Hypena scabra* Fabricius (green cloverworm); *Hyponeuma taltula* Schaus; (*Mamestra configurata* Walker (bertha armyworm); *M. brassicae* Linnaeus (cabbage moth); *Melanchra picta* Harris (zebra caterpillar); *Mocis latipes* Guenée (small mocis moth); *Pseudaletia unipuncta* Haworth (armyworm); *Pseudoplusia includens* Walker (soybean looper); *Richia albicosta* Smith (Western bean cutworm); *Spodoptera frugiperda* J E Smith (fall armyworm); *S. exigua* Hübner (beet armyworm); *S. litura* Fabricius (tobacco cutworm, cluster caterpillar); *Trichoplusia ni* Hübner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stem borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea flavipennella* Box; *D. grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hübner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hübner (European corn borer); *Plodia interpunctella* Hübner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit tortrix moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermüller (European grape vine moth); *Platynota flavedana* Clemens (variegated leafroller); *P. stultana* Walsingham (omnivorous leafroller); *Spilonota ocellana* Denis & Schiffermuller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Telchin licus* Drury (giant sugarcane borer); *Thaumetopoea pityocampa* Schiffermuller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (Diaprepes root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *S. livis* Vaurie (sugarcane weevil); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape colaspis); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae*

Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis* rugiceps LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

Adults and immatures of the order Diptera are of interest, including leafminers *Agromyza parvicornis* Loew (corn blotch leafminer); midges including, but not limited to: *Contarinia sorghicola* Coquillett (sorghum midge); Mayetiola destructor Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are those of the order Hemiptera such as, but not limited to, the following families: Adelgidae, Aleyrodidae, Aphididae, Asterolecaniidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); *Blostomatidae* spp.; *Brevicoryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); *Cimicidae* spp.; *Coreidae* spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schäffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *M. posticata* Stål (little cicada of sugarcane); *Melanaphis sacchari* Zehntner (sugarcane aphid); *Melanaspis glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); *Pyrrhocoridae* spp.; *Quadraspidiotus perniciosus* Comstock (San Jose scale); *Reduviidae* spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Scaptocoris castanea* Perty (brown root stink bug); *Schizaphis graminum* Rondani (greenbug); *Sipha flava* Forbes (yellow sugarcane aphid); *Sitobion avenae* Fabricius (English grain aphid); *Sogatella furcifera* Horvath (whitebacked planthopper); *Sogatodes oryzicola* Muir (rice delphacid); *Spanagonicus albofasciatus* Reuter (whitemarked fleahopper); *Therioaphis maculata* Buckton (spotted alfalfa aphid); *Tinidae* spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as *Aceria tosichella* Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as Lepisma saccharina Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cornitermes cumulans* Kollar, *Cylindrotermes nordenskioeldi* Holmgren and *Pseudacanthotermes militaris* Hagen (sugarcane termite); as well as those in the Rhinotermitidae family including, but not limited to *Heterotermes tenuis* Hagen. Insects of the order Thysanoptera are also of interest, including but not limited to thrips, such as *Stenchaetothrips minutus* van Deventer (sugarcane thrips).

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

EXAMPLES

Example 1. Transformation of Maize by *Agrobacterium* Transformation and Regeneration of Transgenic Plants Containing the Cry1F, Cry34Ab1, Cry35Ab1 (Cry34/35Ab1) and Pat Genes 4114 maize was produced by *Agrobacterium*-mediated transformation with plasmid PHP27118. This event contains the cry1F, cry34Ab1, cry35Ab1, and pat gene cassettes, which confer resistance to certain lepidopteran and coleopteran pests.

Specifically, the first cassette contains a truncated version of the cry1F gene from Bt var. aizawai. The insertion of the cry1F gene confers resistance to damage by lepidopteran pests, including ECB and FAW. The Cry1F protein (SEQ ID NO: 1) is comprised of 605 amino acids and has a molecular weight of approximately 68 kDa. The expression of the cry1F gene is controlled by the maize polyubiquitin promoter (Christensen et al., 1992, supra), providing constitutive expression of Cry1F protein in maize. This region also includes the 5' UTR and intron associated with the native polyubiquitin promoter. The terminator for the cry1F gene is the poly(A) addition signal from open reading frame 25 (ORF 25) of the *Agrobacterium tumefaciens* (*A. tumefaciens*) Ti plasmid pTi15955 (Barker et al., 1983, supra).

The second cassette contains the cry34Ab1 gene isolated from Bt strain PS149B1 (U.S. Pat. Nos. 6,127,180; 6,624,145 and 6,340,593). The Cry34Ab1 protein (SEQ ID NO: 2) is 123 amino acid residues in length and has a molecular weight of approximately 14 kDa. The expression of the cry34Ab1 gene is controlled by a second copy of the maize polyubiquitin promoter with 5' UTR and intron (Christensen et al., 1992, supra). The terminator for the cry34Ab1 gene is the pinII terminator (Keil et al., 1986, supra; An et al., 1989, supra).

The third gene cassette contains the cry35Ab1 gene, also isolated from Bt strain PS149B1 (U.S. Pat. Nos. 6,083,499; 6,548,291 and 6,340,593). The Cry35Ab1 protein (SEQ ID NO: 3) has a length of 383 amino acids and a molecular weight of approximately 44 kDa. Simultaneous expression of the Cry34Ab1 and Cry35Ab1 proteins in the plant confers resistance to coleopteran insects, including WCRW. The expression of the cry35Ab1 gene is controlled by the Triticum aestivum (wheat) peroxidase promoter and leader sequence (Hertig et al. 1991, supra). The terminator for the cry35Ab1 gene is a second copy of the pinII terminator (Keil et al. 1986, supra; An et al. 1989, supra).

The fourth and final gene cassette contains a version of pat from *Streptomyces viridochromogenes* that has been optimized for expression in maize. The pat gene expresses PAT, which confers tolerance to phosphinothricin (glufosinate-ammonium). The PAT protein (SEQ ID NO: 4) is 183 amino acids residues in length and has a molecular weight of approximately 21 kDa. Expression of the pat gene is controlled by the promoter and terminator regions from the CaMV 35S transcript (Franck et al., 1980, supra; Odell et al., 1985, supra; Pietrzak, et al., 1986, supra). Plants containing the DNA constructs are also provided. A description of the genetic elements in the PHP27118 T-DNA (set forth in SEQ ID NO: 5) and their sources are described further in Table 1.

TABLE 1

Genetic Elements in the T-DNA Region of Plasmid PHP27118

| Location on T-DNA (bp position) | Genetic Element | Size (bp) | Description |
|---|---|---|---|
| 1 to 25 | Right Border | 25 | T-DNA RB region from Ti plasmid of *A. tumefaciens* |
| 26 to 76 | Ti Plasmid Region | 51 | Non-functional sequence from Ti plasmid of *A. tumefaciens* |
| 77 to 114 | Polylinker Region | 38 | Region required for cloning genetic elements |
| 115 to 1014 | ubiZM1 Promoter | 900 | Promoter region from *Zea mays* polyubiquitin gene (Christensen et al., 1992, supra) |
| 1015 to 1097 | ubiZM1 5' UTR | 83 | 5' UTR from *Zea mays* polyubiquitin gene. Id. |
| 1098 to 2107 | ubiZM1 Intron | 1010 | Intron region from *Zea mays* polyubiquitin gene. Id. |
| 2108 to 2129 | Polylinker Region | 22 | Region required for cloning genetic elements |
| 2130 to 3947 | cty1F Gene | 1818 | Truncated version of cry1F from *Bt* var. *aizawai* |
| 3948 to 3992 | Polylinker Region | 45 | Region required for cloning genetic elements |
| 3993 to 4706 | ORF 25 Terminator | 714 | Terminator sequence from *A. tumefaciens* pTi15955 ORF 25 (Barker et al., 1983, supra) |
| 4707 to 4765 | Polylinker Region | 59 | Region required for cloning genetic elements |
| 4766 to 5665 | ubiZM1 Promoter | 900 | Promoter region from *Zea mays* polyubiquitin gene (Christensen et al., 1992, supra) |
| 5666 to 5748 | ubiZM1 5' UTR | 83 | 5' UTR from *Zea mays* polyubiquitin gene. Id. |
| 5749 to 6758 | ubiZM1 Intron | 1010 | Intron region from *Zea mays* polyubiquitin gene. Id. |
| 6759 to 6786 | Polylinker Region | 28 | Region required for cloning genetic elements |
| 6787 to 7158 | cry34Ab1 Gene | 372 | Synthetic version of cry34Ab1 encoding 14 kDa delta-endotoxin parasporal crystal protein from the nonmotile strain PS149B1 of *Bt* (Moellenbeck et al. (2001) *Nature Biotech.* 19:668-672; Ellis et al. (2002) *Appl. Env. Microbiol.* 68(3): 1137-1145; Herman et al. (2002) *Environ. Entomol.* 31(2): 208-214.) |
| 7159 to 7182 | Polylinker Region | 24 | Region required for cloning genetic elements |
| 7183 to 7492 | pinII Terminator | 310 | Terminator region from *Solanum tuberosum* proteinase inhibitor II gene (Keil et al. 1986, supra; An et al. 1989, supra) |
| 7493 to 7522 | Polylinker Region | 30 | Region required for cloning genetic elements |
| 7523 to 8820 | TA Peroxidase Promoter | 1298 | Promoter from *Triticum aestivum* peroxidase including leader sequence (Hertig et al. 1991, supra) |
| 8821 to 8836 | Polylinker Region | 16 | Region required for cloning genetic elements |
| 8837 to 9988 | cry35Ab1 | 1152 | Synthetic version of cry35Ab1 encoding a 44 kDa delta-endotoxin parasporal crystal protein from the nonmotile strain PS149B1 of Bt (Moellenbeck et al. 2001, supra; Ellis et al. 2002, supra; Herman et al. 2002, supra) |
| 9989 to 10012 | Polylinker Region | 24 | Region required for cloning genetic elements |
| 10013 to 10322 | pinII Terminator | 310 | Terminator region from *Solanum tuberosum* proteinase inhibitor II gene (Keil et al. 1986, supra; An et al. 1989, supra) |
| 10323 to 10367 | Polylinker Region | 45 | Region required for cloning genetic elements |
| 10368 to 10897 | CaMV 35S Promoter | 530 | 35S promoter from CaMV (Franck et al., 1980, supra; Odell et al., 1985, supra; Pietrzak, et al., 1986, supra) |
| 10898 to 10916 | Polylinker Region | 19 | Region required for cloning genetic elements |
| 10917 to 11468 | pat Gene | 552 | Synthetic, plant-optimized phosphinothricin acetyltransferase coding sequence from *Streptomyces viridochromogenes.* |
| 11469 to 11488 | Polylinker Region | 20 | Region required for cloning genetic elements |
| 11489 to 11680 | CaMV35S Terminator | 192 | 35S terminator from CaMV (Franck et al., 1980, supra; Pietrzak, et al., 1986, supra) |
| 11681 to 11756 | Polylinker Region | 76 | Region required for cloning genetic elements |

TABLE 1-continued

Genetic Elements in the T-DNA Region of Plasmid PHP27118

| Location on T-DNA (bp position) | Genetic Element | Size (bp) | Description |
|---|---|---|---|
| 11757 to 11953 | Ti Plasmid Region | 197 | Non-functional sequence from Ti plasmid of *A. tumefaciens* |
| 11954 to 11978 | Left Border | 25 | T-DNA LB region from Ti plasmid of *A. tumefaciens* |

Figure 2:
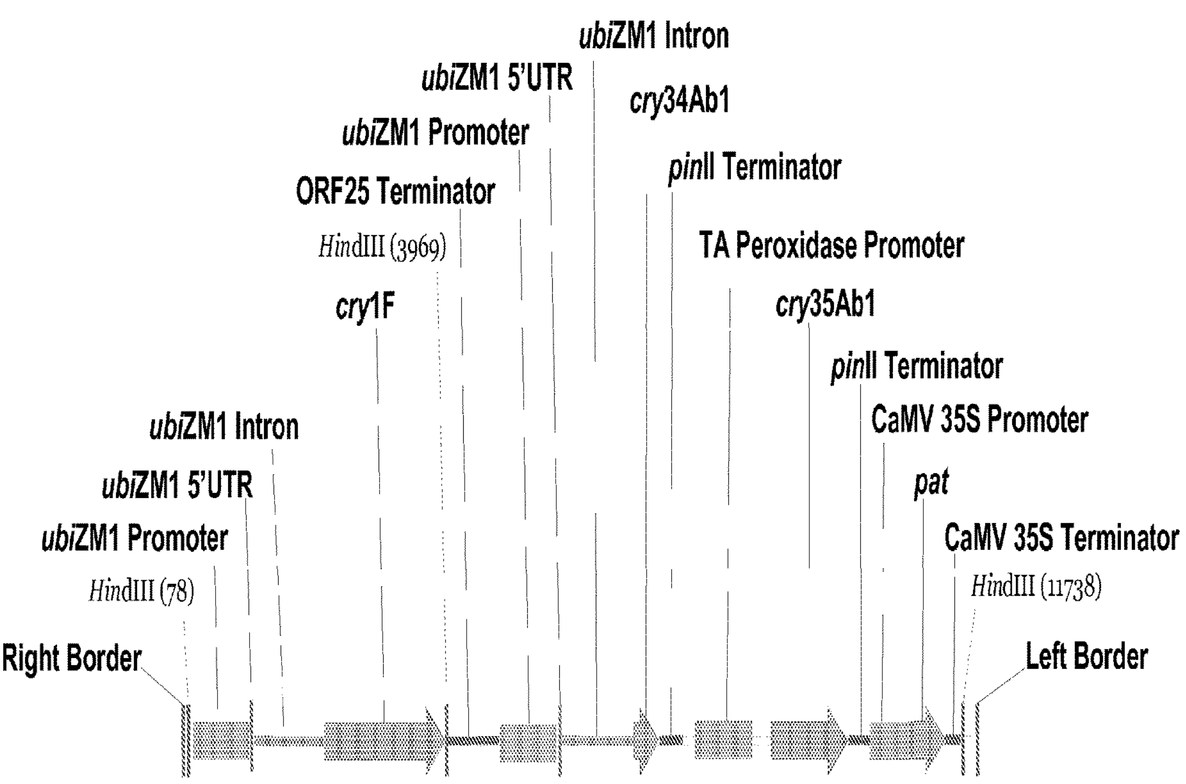
FIG. 2. Schematic diagram of the T-DNA indicating the cry1F, cry34Ab1, cry35Ab1, and pat genes (arrows) along with their respective regulatory elements. Hind III restriction enzyme sites within the T-DNA are indicated. The size of the T-DNA is 11978 bp.

Immature embryos of maize (*Zea mays* L.) were aseptically removed from the developing caryopsis nine to eleven days after pollination and inoculated with *A. tumefaciens* strain LBA4404 containing plasmid PHP27118 (FIG. 1), essentially as described in Zhao (U.S. Pat. No. 5,981,840, the contents of which are hereby incorporated by reference). The T-DNA region of PHP27118 is shown in FIG. 2. After three to six days of embryo and *Agrobacterium* co-cultivation on solid culture medium with no selection, the embryos were then transferred to a medium without herbicide selection but containing carbenicillin. After three to five days on this medium, embryos were then transferred to selective medium that was stimulatory to maize somatic embryogenesis and contained bialaphos for selection of cells expressing the pat transgene. The medium also contained carbenicillin to kill any remaining *Agrobacterium*. After six to eight weeks on the selective medium, healthy, growing calli that demonstrated resistance to bialaphos were identified. The putative transgenic calli were subsequently regenerated to produce T0 plantlets.

Samples were taken from the T0 plantlets for PCR analysis to verify the presence and copy number of the inserted cry1F, cry35Ab1, cry34Ab1, and/or pat genes. Maize event DP-004114-3 was confirmed to contain a single copy of the T-DNA (See Examples 2 and 3). In addition to this analysis, the T0 plantlets were analyzed for the presence of certain *Agrobacterium* binary vector backbone sequences by PCR (data not shown). Plants that were determined to be single copy for the inserted genes and negative for *Agrobacterium* backbone sequences were selected for further greenhouse propagation. These selected T0 plants were screened for trait efficacy and protein expression by conducting numerous bioassays (See Example 5). The T0 plants meeting all criteria were advanced and crossed to inbred lines to produce seed for further testing. A schematic overview of the transformation and event development is presented in FIG. 3.

Example 2. Characterization of Maize Event DP-004114-3

Genomic DNA from leaf tissue of test seed from 4114 maize and a control substance (seed from a non-genetically modified maize with a genetic background representative of the event background) was isolated and subjected to qualitative PCR amplification using a construct-specific primer pair. The PCR products were separated on an agarose gel to confirm the presence of the inserted construct in the genomic DNA isolated from the test seed, and the absence of the inserted construct in the genomic DNA isolated from the control seed. A reference standard (Low DNA Mass Ladder; Invitrogen Corporation Catalog #10380-012) was used to determine the PCR product size. The reliability of the construct-specific PCR method was assessed by repeating the experiment three times. The sensitivity of the PCR amplification was evaluated by various dilutions of the genomic DNA from 4114 maize.

Test and control leaf samples (V5-V7 leaf stage) were harvested from plants grown at the DuPont Experimental Station (Wilmington, DE) from seed obtained from Pioneer Hi-Bred (Johnston, IA). Genomic DNA extractions from the test and control leaf tissues were performed using a standard urea extraction protocol.

Genomic DNA was quantified using the NanoDrop 1000 Spectrophotometer using ND-1000 V3.6 Software (ThermoScientific, Wilmington, DE) and the Quant-iT PicoGreen® reagent (Invitrogen, Carslbad, CA). DNA samples were visualized on an agarose gel to confirm quantitation values and to determine the DNA quality.

Genomic DNA samples isolated from leaf tissue of 4114 maize and control samples were subjected to PCR amplification (Roche High Fidelity PCR Master Kit, Roche Catalog #12140314001) utilizing a construct-specific primer pair (SEQ ID NOs: 7 and 8) which spans the maize ORF 25 terminator and the ubiquitin promoter (See FIG. 2), and allows for the unique identification of the inserted T-DNA in 4114 maize. A second primer set (SEQ ID NOs: 9 and 10) was used to amplify the endogenous maize invertase gene (GenBank accession number AF171874.1) as a positive control for PCR amplification. The PCR target site and size of the expected PCR product for each primer set are shown in Table 2. PCR reagents and reaction conditions are shown in Table 3. In this study, 50 ng of leaf genomic DNA was used in all PCR reactions.

TABLE 2

PCR Genomic DNA Target Site and Expected Size of PCR Products

| Primer Set | Target Site | Expected Size of PCR Product (bp) |
|---|---|---|
| SEQ ID NO: 7 & 8 | Construct Specific T-DNA: ORF 25 terminator and ubiquitin promoter | 287 |
| SEQ ID NO: 9 & 10 | Endogenous maize invertase gene | 225 |

TABLE 3

PCR Reagents and Reaction Conditions

| PCR Reagents | | PCR Reaction Conditions | | | |
|---|---|---|---|---|---|
| Reagent | Volume (μL) | Cycle Element | Temp (° C.) | Time (sec) | # Cycles |
| Template DNA (25 ng/μL) | 2 | Initial Denaturation | 94 | 120 | 1 |
| Primer 1 (10 μM) | 2 | Denaturation | 94 | 10 | 35 |
| Primer 2 (10 μM) | 2 | Annealing | 65 | 15 | |
| PCR Master Mix* | 25 | Elongation | 68 | 60 | |

TABLE 3-continued

| PCR Reagents and Reaction Conditions | | | | | |
|---|---|---|---|---|---|
| PCR Reagents | | PCR Reaction Conditions | | | |
| Reagent | Volume (μL) | Cycle Element | Temp (° C.) | Time (sec) | # Cycles |
| $ddH_2O$ | 19 | Final Elongation | 68 | 420 | 1 |
| — | — | Hold Cycle | 4 | Until analysis | — |

$ddH_2O$: double-distilled water
*Roche High Fidelity Master Mix

A PCR product of approximately 300 bp in size amplified by the construct-specific primer set (SEQ ID NOs: 7 and 8) was observed in PCR reactions using plasmid PHP27118 (10 ng) as a template and all 4114 maize DNA samples, but absent in all control maize samples and the no-template control. This experiment was repeated three times, and similar results were obtained. Results observed for DNA extracts from five 4114 maize plants and five control maize plants corresponded closely with the expected PCR product size (287 bp) for samples containing 4114 maize genomic DNA. A PCR product approximately 220 bp in size was observed for both 4114 maize and control maize samples following PCR reaction with the primer set (SEQ ID NOs: 9 and 10) for detection of the endogenous maize invertase gene. These results corresponded closely with the expected PCR product size (225 bp) for genomic DNA samples containing the maize endogenous invertase gene. The endogenous target band was not observed in the no-template control.

In order to assess the sensitivity of the PCR amplification, various concentrations of a single DNA sample from 4114 maize were diluted in non-genetically modified control DNA, resulting in 4114 maize DNA amounts ranging from 500 fg, 5 pg, 10 pg, 50 pg, 100 pg, 5 00 pg, 5 ng, and 50 ng (the total amount of genomic DNA in all PCR samples was 50 ng). Each dilution was subjected to PCR amplification as previously conducted. Based on this analysis, the limit of detection (LOD) was determined to be approximately 100 pg of 4114 maize DNA in 50 ng of total DNA, or 0.2% 4114 maize DNA.

In conclusion, qualitative PCR analysis utilizing a construct-specific primer set for 4114 maize confirmed that the test plants contained the inserted T-DNA from plasmid PHP27118, as evident by the presence of the construct-specific target band in all test plant samples analyzed, and the absence in the non-genetically modified control plants. This result was reproducible. Test and control plants both contained the endogenous maize invertase gene. The sensitivity of the analysis under the conditions described is approximately 100 pg of 4114 maize genomic DNA in 50 ng of total genomic DNA or 0.2% 4114 maize genomic DNA.

Example 3. Southern Blot Analysis of DP-004114-3 Maize for Integrity and Copy Number Southern blot analysis was used to confirm the integrity and copy number of the inserted T-DNA from PHP27118 and to confirm the presence of the cry1F, cry34Ab1, cry35Ab1, and pat gene cassettes in 4114 maize.

Five individual plants from the T1 generation of 4114 maize were selected for Southern blot analysis. Young leaf material was harvested from the 4114 maize (test) and non-transgenic maize (control) plants and was immediately placed on dry ice. The frozen samples were lyophilized and genomic DNA was extracted from the test and control tissues using a CTAB extraction method.

Following restriction enzyme digestions as detailed below, the DNA fragments were separated on agarose gels, depurinated, denatured, and neutralized in situ, and transferred to a nylon membrane in 20x SSC buffer using the method as described for TURBOBLOTTER™ Rapid Downward Transfer System (Schleicher & Schuell). Following transfer to the membrane, the DNA was bound to the membrane by ultraviolet light crosslinking.

Integrity

The restriction enzyme Hind III was selected for Southern analysis of integrity, as there are three sites located within the T-DNA (FIG. 2). Approximately 1-3 μg of genomic DNA was digested with Hind III and separated by size on an agarose gel. As a positive control, approximately 15 pg of plasmid containing the PHP27118 T-DNA was spiked into a control plant DNA sample, digested and included on the agarose gel. A negative control was also included to verify background hybridization of the probe to the maize genome.

Four probes homologous to the cry1F, cry34Ab1, cry35Ab1, and pat genes on the PHP27118 T-DNA (for gene elements, see FIG. 2) were used for hybridization to confirm the presence of the genes. In order to develop the probes, fragments homologous to the cry1F, cry34Ab1, cry35Ab1, and pat genes were generated by PCR from plasmid containing the PHP27118 T-DNA, size separated on an agarose gel, and purified using a QIAquick® gel extraction kit (Qiagen). All DNA probes were subsequently generated from the fragments using the Rediprime™ II DNA Labeling System (Amersham) which performs random prime labeling with [$^{32}$P]dCTP.

The labeled probes were hybridized to the target DNA on the nylon membranes for detection of the specific fragments using the MiracleHyb® Hybridization Solution essentially as described by the manufacturer (Stratagene). Washes after hybridization were carried out at high stringency. Blots were exposed to X-ray film at −80° C. for one or more time points to detect hybridizing fragments.

Because the Hind III enzyme sites were known within the T-DNA, exact expected band sizes were determined for each of the probes (Table 4, FIG. 2). For an intact copy of the T-DNA, the cry1F probe was expected to hybridize to a fragment of 3891 bp. The cry34Ab1, cry35Ab1, and pat gene probes were expected to hybridize to a fragment of 7769 bp. Fragments from the test samples matching the expected sizes, as well as matching the bands in the plasmid control sample, would confirm the integrity of the inserted T-DNA and the presence of each gene.

The results of the Southern blot analysis with Hind III and the cry1F, cry34Ab1, cry35Ab1, and pat gene probes confirmed the expected fragment sizes and, thus, confirmed that the T-DNA inserted intact into each of the events and that each of the genes was present.

A band of approximately 4 kb was observed with the cry1F probe which is consistent with the expected fragment size. A similar fragment of approximately 4 kb was observed in the plasmid positive control lane, which was presumed to be the expected band of 3891 bp. Based on equivalent migration of the hybridizing band in the events to the band in the plasmid positive control, it was confirmed that the portion of the T-DNA containing cry1F had inserted intact in 4114 maize.

In the hybridization with the cry34Ab1 probe, a band of approximately 8 kb was observed in the event and also in the plasmid positive control. The hybridizing band in the plasmid positive control lane was presumed to be the expected band of 7769 bp. Because the hybridizing band in the event had migrated equivalently with this band, it was confirmed that this portion of the T-DNA containing cry34Ab1 was inserted intact.

Similarly, hybridizations with cry35Ab1 and pat hybridized to the same 7769 bp fragment in the plant and plasmid positive control as expected. These results confirmed that the portion of the T-DNA containing the cry35Ab1 and pat genes had inserted intact.

This Southern blot analysis confirms that 4114 maize contains an intact copy of the T-DNA from PHP27118 containing the cry1F, cry34Ab1, cry35Ab1, and pat genes.

TABLE 4

Summary of Expected and Observed Hybridization Fragments on Southern Blots for 4114 Maize DNA digested with Hind III

| Probe | Expected Fragment Size from PHP27118 T-DNA (bp)[1] | Observed Fragment Size (kb) [2] |
|---|---|---|
| cry1F | 3891 | ~4 |
| cry34Ab1 | 7769 | ~8 |
| cry35Ab1 | 7769 | ~8 |
| pat | 7769 | ~8 |

[1]Expected fragment sizes based on map of PHP27118 T-DNA (FIG. 2).

[2] All observed fragments migrated equivalently with the plasmid positive control and, therefore, were confirmed to represent the intact portion of the PHP27118 T-DNA.

Copy Number

The cry1F and pat probes were used in Southern blot hybridizations to evaluate the copy number of the insertions in 4114 maize.

The restriction enzyme Bcl I was selected for Southern analysis of copy number, as there is a single site located within the T-DNA (FIG. 2). Approximately 3 μg of genomic DNA from individual plants of the T1 generation of event 4114 was digested with Bcl I and separated by size on an agarose gel. A plasmid containing the PHP27118 T-DNA was spiked into a control plant DNA sample, digested and included on the agarose gel to serve as a positive hybridization control. Negative control maize DNA was also included to verify background hybridization of the probe to the maize genome. DNA Molecular Weight Marker VII, digoxigenin (DIG) labeled (Roche, Indianapolis, IN), was included on Bcl I blots as a size standard for hybridizing fragments.

Probes for the cry1F and pat genes were also labeled by a PCR reaction incorporating a digoxigenin (DIG) labeled nucleotide, [DIG-11]-dUTP, into the fragment. PCR labeling of isolated fragments was carried out according to the procedures supplied in the PCR DIG Probe Synthesis Kit (Roche).

The DIG-labeled probes were hybridized to the Bcl I Southern blots of the T1 generation of the 4114 event. Probes were hybridized to the target DNA for detection of the specific fragments using DIG Easy Hyb solution (Roche) essentially as described by manufacturer. Post-hybridization washes were carried out at high stringency. DIG-labeled probes hybridized to the bound fragments were detected using the CDP-Star Chemiluminescent Nucleic Acid Detection System (Roche). Blots were exposed to X-ray film at room temperature for one or more time points to detect hybridizing fragments. Membranes were stripped of hybridized probe following the manufacturer's recommendation prior to hybridization with additional probes.

The restriction enzyme Bcl I, having a single restriction site within the T-DNA (FIG. 2), was selected to confirm the presence of a single PHP27118 T-DNA insertion in 4114 maize. The site for Bcl I is located at bp 2546 of the T-DNA (FIG. 2) and will yield fragments of greater than about 2500 bp and 9400 bp for a single inserted T-DNA. Hybridization with the pat probe would indicate the number of copies of this element found in the event based on the number of hybridizing bands (e.g., one hybridizing band indicates one copy of the element). The pat probe would hybridize to the fragment of greater than 9400 bp. Because the Bcl I restriction enzyme site is within the cry1F gene, the cry1F probe is expected to hybridize to both fragments and result in two bands for a single T-DNA insertion (FIG. 2).

The results of the Southern blot analysis with Bcl I and the cry1F and pat gene probes for 4114 maize are summarized in Table 5.

TABLE 5

Summary of Expected and Observed Hybridization Fragments on Southern Blots for Bcl I digests of 4114 Maize

| Probe | Enzyme Digest | Expected Fragment Size from PHP27118 T-DNA (bp)[1] | Observed Fragment Size (kb)[2] |
|---|---|---|---|
| cry1F | Bcl I | >2500[3] | ~3.1 |
| | | >9400 | >8.6 |
| pat | Bcl I | >9400 | >8.6 |

[1]Expected fragment sizes based on map of PHP27118 T-DNA (FIG. 2).

[2]All observed fragment sizes are approximated based on the migration of the DIG VII molecular weight marker.

[3]Two fragments are expected with the cry1F probe due to the location of the Bcl I restriction site within the cry1F gene.

The results of the Southern blot analysis of 4114 maize with Bcl I digestion and the cry1F probe showed two bands as expected, one band of greater than 8.6 kb and a second band of approximately 3.1 kb. Two bands are expected for a single insertion due to the location of the Bcl I site within the cry1F gene, so these results indicate that there is a single copy of cry1F in 4114 maize. The results of the Southern blot analysis of 4114 maize with Bcl I digestion and the pat probe showed a single band of greater than 8.6 kb that matched the size of the larger cry1F band as expected. These results indicate that there is also a single insertion of the pat gene in maize event 4114.

As the cry34Ab1 and cry35Ab1 genes are located on the same fragment as the pat gene and part of the cry1F gene, and between the cry1F and pat genes on the T-DNA, by extension this also demonstrates that this event is likely to contain a single copy of each of these genes.

Example 4. Sequencing Characterization of Insert and Genomic Border Regions of Maize Event DP-004114-3

The sequence of the insert and genomic border regions was determined to confirm the integrity of the inserted DNA and to characterize the genomic sequence flanking the insertion site present in 4114 maize. In total, 16,752 bp of 4114 maize genomic sequence was confirmed, comprising 2,422 bp of the 5' genomic border sequence, 2,405 bp of the 3' genomic border sequence, and 11,925 bp of inserted T-DNA from PHP27118. The inserted T-DNA in 4114 maize was found to have a 29 bp deletion on the Right Border (RB) end and a 24 bp deletion on the Left Border (LB) end. All remaining sequence is intact and identical to that of plasmid PHP27118. The 5' and 3' genomic border regions of 4114 maize were verified to be of maize origin by PCR amplification and sequencing of the genomic border regions from both 4114 maize and control maize plants.

Seed containing event DP-004114-3 was obtained from a T1S2 generation of 4114 maize. Control seed was obtained from a maize line that has a similar genetic background to 4114 maize but does not contain the cry1F, cry34Ab1, cry35Ab1, and pat gene cassettes. All seeds were obtained from Pioneer Hi-Bred International, Inc. (Johnston, IA). The Low DNA Mass Ladder (Invitrogen Corp., Carlsbad, CA) and the High DNA Mass Ladder (Invitrogen Corp.) were used for gel electrophoresis to estimate DNA fragment sizes on agarose gels.

The 4114 maize seed and the control seed were planted in growth chambers at the DuPont Experimental Station (Wilmington, DE) to produce plant tissues used for this study. One seed was planted per pot, and the pot was uniquely identified. All plants were grown with light, temperature, and water regulated for healthy plant growth. Leaf samples were collected from the control and 4114 maize plants. For each individual plant, leaf material was collected in a pre-labeled bag, placed on dry ice, and then transferred to an ultra low freezer (<−55° C.) following collection. All samples were maintained frozen until tissue processing.

Genotype Confirmation via Event-Specific PCR Analysis

A leaf sample was taken from all test and control plants for event-specific PCR analysis. DNA was extracted from each leaf sample using the Extract-N-Amp™ Plant PCR kit following the described procedure (Sigma-Aldrich, St. Louis, MO) for real-time PCR analysis.

Real-time PCR was performed on each DNA sample utilizing an ABI PRISM® 7500HT Sequence Detection System (Applied Biosystems, Inc., Foster City, CA). TaqMan® probe (Applied Biosystems, Inc.) and primer sets (Integrated DNA Technologies, Coralville, IA) were designed to detect a target sequence from 4114 maize. In addition, a second TaqMan® probe and primer set for a reference maize endogenous gene was used to confirm the presence of amplifiable DNA in each reaction. The analysis consisted of real-time PCR determination of qualitative positive/negative calls. The extracted DNA was assayed using TaqMan® Universal PCR Master Mix, No AmpErase® UNG (Applied Biosystems, Inc.).

Positive or negative determination for 4114 maize was based on comparison of the CT (threshold cycle) of the event-specific target PCR to that of the maize endogenous reference target. If the event and endogenous PCR targets amplified above CT threshold, then the plant was scored as positive for that event. If the endogenous target amplified and the event target did not, then the plant was scored as negative. If neither target amplified for a particular sample, then it was determined to be a poor quality DNA sample or failed run and the assay was repeated.

All 4114 maize plants were positive for the event-specific PCR and the PAT, Cry1F, and Cry34Ab1 proteins, whereas all the control maize plants were negative. The results are summarized in Table 6.

TABLE 6

Summary of Event-Specific PCR Analysis and Cry1F, Cry34Ab1, and PAT Protein Expression in 4114 Maize and Control Maize Plants

| | Event-Specific PCR[1] | Cry1F[2] | Cry34Ab1[2] | PAT[2] |
|---|---|---|---|---|
| 4114 Maize Plant ID | | | | |
| T-F-08-233C-1 | + | + | + | + |
| T-F-08-233C-2 | + | + | + | + |
| T-F-08-233C-3 | + | + | + | + |
| T-F-08-233C-4 | + | + | + | + |
| Control Maize Plant ID | | | | |
| C-F-08-246C-1 | − | − | − | − |
| C-F-08-246C-2 | − | − | − | − |

[1]Summary of event-specific real time PCR assay for 4114 maize. Positive (+) indicates the presence of 4114 maize event. Negative (−) indicates the absence of 4114 maize event.

[2]Summary of Cry1F, Cry34Ab1, and PAT protein expression in 4114 maize and control maize plants using lateral flow devices. Positive (+) indicates the presence of the protein. Negative (−) indicates the absence of the protein.

DNA Sequencing

DNA fragments were cloned and submitted for sequencing at the Pioneer Crop Genetics Research sequencing facility (Wilmington, DE). Sequencher™ software from Gene Codes Corporation (Ann Arbor, Michigan) was used to assemble the sequences. Sequence annotation was performed using Vector NTI 9.1.0 (Invitrogen Corp) by comparing the T-DNA insert sequences generated from 4114 maize with the sequences from the T-DNA region of plasmid PHP27118 (used for transformation to produce 4114 maize).

The T-DNA region of plasmid PHP27118, used to create 4114 maize, was sequenced and compared with the inserted T-DNA sequence in 4114 maize.

The sequence of the T-DNA region of plasmid PHP27118 was used to design primer pairs to characterize the inserted T-DNA in 4114 maize. Six overlapping PCR products were generated using genomic DNA from four different 4114 maize plants as template. These PCR products were cloned and sequenced.

Sequencing of 5' and 3' Flanking Genomic Border Regions

Preliminary sequence characterization of the 5' and 3' flanking genomic border regions were carried out using several rounds of inverse PCR, (Silver and Keerikatte (1989) *J. Virol.* 63: 1924; Ochman et al. (1988) *Genetics* 120:621-623; Triglia et al., (1988) *Nucl. Acids Res.* 16:8186) with primers anchored within various regions of the inserted T-DNA. Sequence information obtained from inverse PCR was subjected to BLASTn analysis and showed a match to the maize BAC clone AC211214 from the NCBI (National Center for Biotechnology Information) GenBank nucleotide database. This sequence was then used to design primers that spanned the 5' and 3' insert/genomic junctions in 4114 maize. The PCR products generated from four 4114 maize plants were cloned and sequenced to verify the 5' and 3' insert/genomic junctions and the genomic border regions.

In addition, to demonstrate that the identified 5' and 3' genomic border regions were of maize origin, PCR was performed on 4114 maize and control maize plants within the genomic regions. Each PCR fragment was directly sequenced to verify its identity of maize origin.

The T-DNA sequence information of plasmid PHP27118 was used to design primers to verify the inserted sequence in 4114 maize (Tables 7 and 8).

TABLE 7

PCR Primers Used to Characterize the Genomic Border Regions and Inserted T-DNA in 4114 Maize

| PCR Fragment | Primer Pair | Primer SEQ ID NOs: | Size (bp) | Amplified Region |
|---|---|---|---|---|
| A | 09-0-3030/09-0-2787 | 11/12 | 2511 | 5' Genomic border region and insert |
| B | 09-0-3036/09-0-3046 | 13/14 | 3622 | Insert |
| C | 09-0-2980/09-0-3045 | 16/15 | 4146 | Insert |
| D | 08-0-2463/08-0-2759 | 17/18 | 2713 | Insert |
| E | 09-0-2775/09-0-3083 | 19/20 | 3062 | Insert |
| F | 09-0-2799/09-0-3005 | 21/22 | 2612 | 3' Genomic border region and insert |
| G | 09-0-3230/09-0-3229 | 23/24 | 257 | 5' Genomic border region |
| H | 09-0-3231/09-0-3084 | 25/26 | 283 | 3' Genomic border region |

TABLE 8

Sequence and Location of Primers Used For PCR Reactions

| PCR Fragment | Primer (SEQ ID NO:) | Primer Sequence (5'-3') | Target Sequence Location (bp to bp)[1] |
|---|---|---|---|
| A | 09-0-3030 (SID: 11) | GAGCATATCCAGCACCAGCTGGTACCAAG | 1-29 |
| | 09-0-2787 (SID: 12) | GCAGGCATGCCCGCGGATA | 2,511-2,493 |
| B | 09-0-3036 (SID: 13) | TGGTCTACCCGATGATGTGATTGGCC | 1,994-2,019 |
| | 09-0-3046 (SID: 14) | CGAAGACAGGATCTGACAAGGTCCGATAG | 5,615-5,587 |
| C | 09-0-3045 (SID: 15) | GACTTCATGAACTCTTTGTTTGTGAC TGCAGAGAC | 5,414-5,414 |
| | 09-0-2980 (SID: 16) | CTCATGACTCAGGACTTGTGGC | 9,559-9,538 |
| D | 08-0-2463 (SID: 17) | ATCAGCCTCTACTTCGAC | 9,390-9,407 |
| | 08-0-2759 (SID: 18) | CTCCATGATCTTCGTCTCATGTG | 12,102-12,080 |
| E | 09-0-2775 (SID: 19) | CACCAACTCCATCCAGAAGTGGC | 11,481-11,503 |
| | 09-0-3083 (SID: 20) | GCCTTGCATTGGCGCAGTGAGAACCG | 14,542-14,517 |
| F | 09-0-2799 (SID: 21) | CGGCGCGCCTCTAGTTGAAGACACGTT | 14,141-14,167 |
| | 09-0-3005 (SID: 22) | CACTGGACTGAGCCGCACAGCTAAGGACAC | 16,752-16,723 |
| G | 09-0-3230 (SID: 23) | GGAACATTCAGACTTGGGAGTCTGGACT | 2,086-2,113 |
| | 09-0-3229 (SID: 24) | GAACAGGGTCCTCGAATCAAGGGCAGC | 2,342-2,316 |
| H | 09-0-3231 (SID: 25) | CGGTTCTCACTGCGCCAATGCAAGGC | 14,517-14,542 |
| | 09-0-3084 (SID: 26) | CATGACGACCATGAAGCAACATC | 14,799-14,777 |

[1]Location in sequence of 4114 Maize.
Bases 1-2,422 = 5' genomic border region
Bases 2,423-14,347 = insert
Bases 14,348-16,752 = 3' genomic border region.

Figure 5:
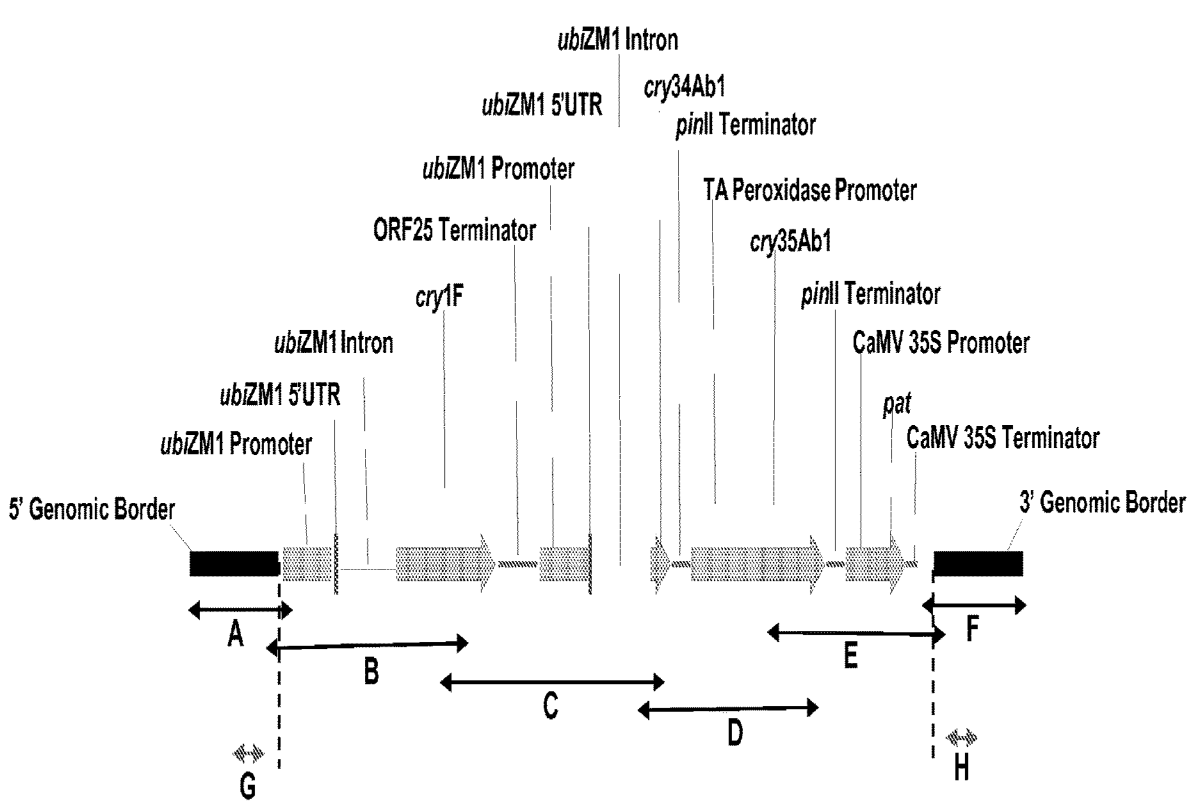
FIG. 5. Schematic representation of the insert and genomic border regions sequenced in 4114 maize. The diagram indicates the PCR fragments generated from 4114 maize genomic DNA that were cloned and sequenced: fragments A through F. The vertical dash line represents the genomic border/insert junctions. Fragment G and H represent the 5' and 3' genomic border regions, respectively. Figure is not drawn to scale.

To characterize the inserted T-DNA in 4114 maize, PCR primers were designed to amplify the T-DNA insert in six separate, overlapping PCR products as outlined in Table 7: fragments A through F (Positions indicated in FIG. 5). As expected, the predicted PCR products were generated only from 4114 maize genomic DNA samples, and were not present in the control maize samples. The six PCR products were cloned and sequenced. When comparing the sequence of the inserted T-DNA in 4114 maize to the T-DNA region of plasmid PHP27118 used to create 4114 maize, it was determined that there was a 29 bp deletion on the RB end, and a 24 bp deletion on the LB end. RB and LB termini deletions often occur in *Agrobacterium*-mediated transformation (Kim et al. (2007) *Plant J.* 51:779-791). All remaining sequence is intact and identical to that of plasmid PHP27118. The sequence of the insertion is presented in SEQ ID NO: 27.

Figure 3:
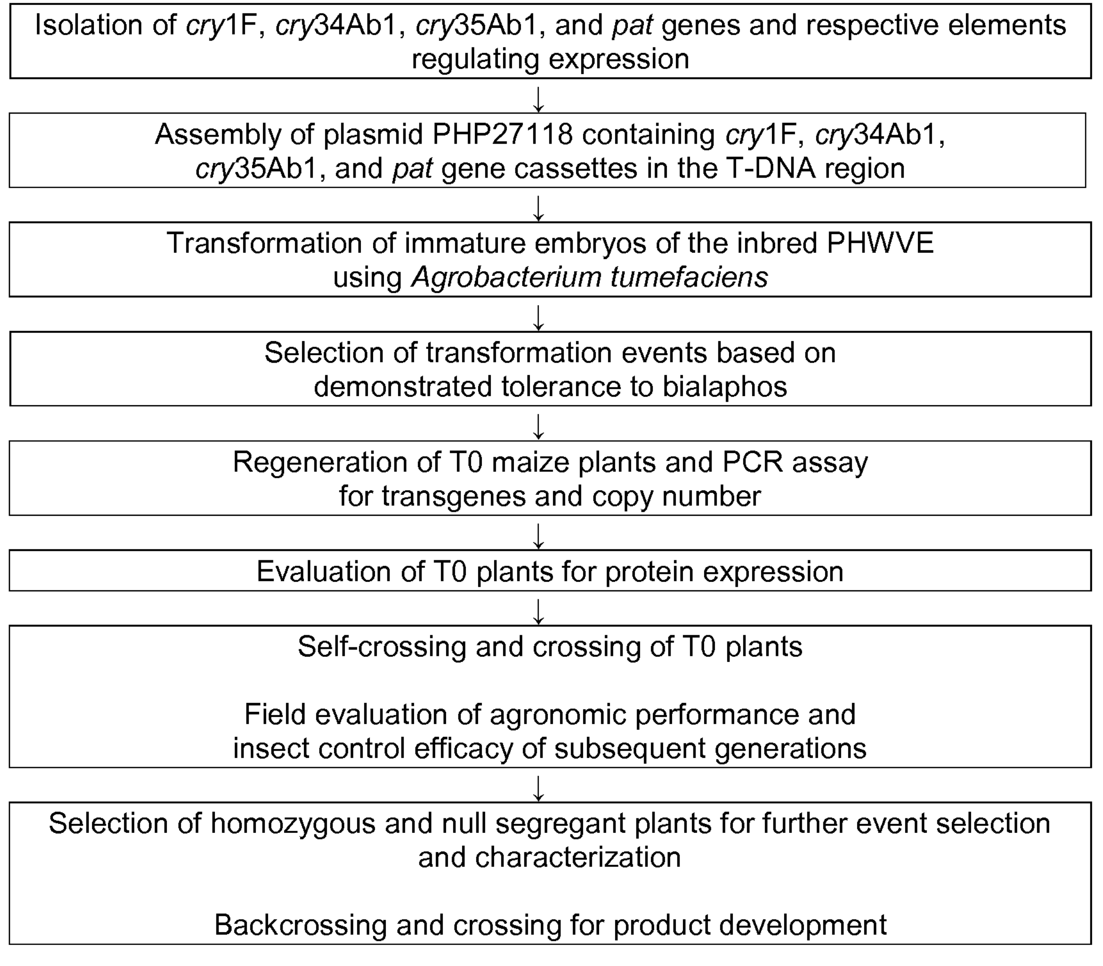
FIG. 3. Schematic Diagram of the Transformation and Development of DP-004114-3.

To verify the additional 5' genomic border sequence, PCR was performed with a forward primer (SEQ ID NO: 11) in the 5' genomic border region and a reverse primer (SEQ ID NO: 12) within the inserted T-DNA. The resulting 2,511 bp PCR fragment A from 4114 maize genomic DNA samples was cloned and sequenced (FIG. 3). The 2,422 bp of the 5' genomic border region sequence is set forth in nucleotides 1-2,422 of SEQ ID NO: 27.

To verify the additional 3' genomic border sequence, PCR was performed with a forward primer (SEQ ID NO: 21) within the inserted T-DNA and a reverse primer (SEQ ID NO: 22) in the 3' genomic border region. The resulting 2,612 bp PCR fragment F from 4114 maize genomic DNA samples was cloned and sequenced (FIG. 3). The 2,405 bp of the 3' genomic border region sequence is set forth in nucleotides 14,348 to 16,752 of SEQ ID NO: 27.

In total, 16,752 bp of sequence from genomic DNA of 4114 maize were confirmed: 2,422 bp of the 5' genomic border sequence, 2,405 bp of the 3' genomic border sequence, and 11,925 bp comprising the inserted T-DNA.

To demonstrate that the identified 5' and 3' flanking genomic border sequences are of maize origin, PCR was performed within the 5' and 3' genomic border regions (the primer pair set forth in SEQ ID NOs: 23 and 24 and the primer pair set forth in SEQ ID NOs: 25 and 26, respectively) on 4114 maize genomic DNA samples and control maize samples. The expected PCR fragment G (257 bp for the 5' genomic region) and PCR fragment H (283 bp for the 3' genomic region) were generated from both 4114 maize and control maize. These PCR products were cloned and sequenced, and the corresponding products from the 4114 maize and the control maize are identical, thus confirming that the sequences are of maize genomic origin.

Example 5. Insect Efficacy of Maize Event DP-004114-3

Efficacy data was generated on 4114 maize. Field testing compared 4114 maize in two genetic backgrounds to a negative control (isoline) in the same backgrounds. Efficacy testing included: first generation ECB (ECB1) foliage damage and second generation ECB (ECB2) stalk damage at four locations, WCRW root damage at three locations, and FAW foliar damage at one location. At each location, single-row plots were planted in a randomized complete block with three replications (20 kernels/plot×12 entries×3 replicates=1 experiment/location). All plants were tissue sampled after emergence to confirm the presence of the event by event-specific PCR. Any negatives were culled and each plot thinned to a target stand of 10-15 evenly spaced plants per plot.

For trials characterizing ECB1 damage, each plant was manually infested with approximately 100 ECB neonate larvae 3 times (300 larvae total) over approximately one week beginning at approximately the V5 growth stage. Approximately three weeks after the last successful infestation, leaf damage ratings (based on a 9-1 visual rating scale where 9 indicates no damage and 1 indicates maximum damage) were taken on 8 consecutive plants per plot (total of 24 plants per genetic background, per entry) and means were calculated for each treatment. First generation ECB foliar feeding results on 4114 maize are shown in Table 9.

TABLE 9

Efficacy of DP-004114-3 Maize Against First Generation ECB Larvae

| Location | Maize Line | Mean ECB1LF Damage Rating ± Standard Error [a,b] |
|---|---|---|
| York, NE | 4114 | 9.0 ± 0.05 A |
| | 1507 × 59122 | 9.0 ± 0.08 A |
| | Negative control | 4.4 ± 0.09 B |
| Johnston, IA | 4114 | 9.0 ± 0.00 A |
| | 1507 × 59122 | 9.0 ± 0.00 A |
| | Negative control | 4.5 ± 0.08 B |
| Mankato, MN | 4114 | 9.0 ± 0.02 A |
| | 1507 × 59122 | 9.0 ± 0.03 A |
| | Negative control | 4.7 ± 0.11 B |
| Princeton, IL | 4114 | 9.0 ± 0.00 A |
| | 1507 × 59122 | 9.0 ± 0.00 A |
| | Negative control | 5.5 ± 0.17 B |

[a] Damage ratings on individual plants were determined using the following visual rating scale:

9. No visible leaf injury or a small amount of pin or fine shot-hole type injury on a few leaves.
8. Small amount of shot-hole type lesions on a few leaves.
7. Shot-hole injury common on several leaves.
6. Several leaves with shot-hole and elongated lesions (Lesions <0.5" in length).
5. Several leaves with elongated lesions (Lesions 0.5" to 1.0" in length).
4. Several leaves with elongated lesions (Lesions >1.0" in length).
3. Long lesions (>1.0") common on about one-half the leaves.
2. Long lesions (>1.0") common on about two-thirds the leaves.
1. Most of the leaves with long lesions.

[b] Within a location, means with the same letter are not significantly different (Fisher's Protected LSD test, P > 0.05).

For trials characterizing ECB2 damage, the same plants infested above for ECB1 were manually infested again later in the growing season with approximately 100 ECB neonate larvae (300 larvae total) per plant 3 times over approximately one week beginning at the R1 growth stage, when approximately 50% of the plants were shedding pollen. At approximately 50-60 days after the last infestation, stalks of 8 consecutive plants per plot (total of 24 plants per genetic background, per entry) were split from the top of the 4th internode above the primary ear to the base of the plant. The total length of ECB stalk tunneling (ECBXCM) was then measured in centimeters and recorded for each plant. Tunnels 1 cm or less were considered entrance holes (larvae was not able to establish in the stalk) and were not included in the total cm of tunneling. Means (total cm of tunneling) were calculated for each treatment. The ECB2 stalk feeding results for 4114 maize are shown in Table 10.

TABLE 10

Efficacy of DP-004114-3 Maize Against Second Generation ECB Larvae

| Location | Maize Line | Mean ECBXCM (tunnel length, cm) ± Standard Error[b] |
|---|---|---|
| York, NE | 4114 | 0.9 ± 0.27 B |
| | 1507 × 59122 | 0.4 ± 0.12 B |
| | Negative control | 22.6 ± 1.83 A |
| Mankato, MN | 4114 | 1.3 ± 0.30 B |
| | 1507 × 59122 | 0.7 ± 0.18 B |
| | Negative control | 31.3 ± 2.19 A |
| Johnston, IA | 4114 | 1.1 ± 0.26 B |
| | 1507 × 59122 | 0.3 ± 0.11 B |
| | Negative control | 33.0 ± 2.51 A |
| Princeton, IL | 4114 | 0.8 ± 0.22 B |
| | 1507 × 59122 | 0.1 ± 0.07 B |
| | Negative control | 10.0 ± 0.94 A |

[b]Within a location, means with the same letter are not significantly different (Fisher's Protected LSD test, P > 0.05).

Root damage caused by WCRW was also investigated. Plants at approximately the V2 growth stage were manually infested with approximately 500 WCRW eggs applied into the soil on each side of the plant (1,000 eggs/plant total). Additionally, plots were planted in fields that had a high probability of containing a natural infestation of WCRW. Plant roots were evaluated at approximately the R2 growth stage. Five consecutive plants per plot (total 45 plants per genetic background, per entry) were removed from the plot and washed with pressurized water. The root damage was rated using the 0-3 node injury scale (CRWNIS) (Oleson, et al. (2005) *J. Econ. Entomol.* 98(1):1-8) and means were calculated for each treatment. Mean root damage ratings from WCRW feeding are shown in Table 11.

TABLE 11

Efficacy of DP-004114-3 Maize Against WCR Larvae

| Location | Maize Line | Mean CRWNIS score ± Standard Error [b,c] |
|---|---|---|
| Johnston, IA | 4114 | 0.1 ± 0.01 B |
| | 1507 × 59122 | 0.1 ± 0.02 B |
| | Negative Control | 0.5 ± 0.09 A |
| Mankato, MN | 4114 | 0.1 ± 0.02 B |
| | 1507 × 59122 | 0.1 ± 0.01 B |
| | Negative Control | 1.1 ± 0.11 A |
| Rochelle, IL | 4114 | 0.3 ± 0.04 B |
| | 1507 × 59122 | 0.1 ± 0.01 B |
| | Negative Control | 1.3 ± 0.18 A |

[b] Damage ratings on individual plant root masses were determined using 0-3 Node Injury Scale (Oleson et al. 2005, supra).

[c] Within a location, means with the same letter are not significantly different (Fisher's Protected LSD test, P > 0.05).

For the FAW efficacy testing, individual plants were manually infested with approximately 75 neonates at approximately the V5 growth stage. Leaves were scored for damage on 8 consecutive plants per plot (total of 24 plants per genetic background, per entry) (FAWLF based on a 9-1 visual rating scale where 9 indicates no damage and 1 indicates maximum damage approximately two weeks after the last successful inoculation and means were calculated for each treatment. Mean damage ratings characterizing FAW foliar feeding on DP-004114-3 are shown in Table 12.

TABLE 12

Efficacy of DP-004114-3 Maize Against FAW Larvae

| Location | Maize Line | Mean FAWLF Damage Rating ± Standard Error[a,b] |
|---|---|---|
| Johnston, IA | 4114 | 8.9 ± 0.06 BC |
| | 1507 × 59122 | 9.0 ± 0.00 A |
| | Negative control | 2.1 ± 0.08 D |

[a]Damage ratings on individual plants were determined using the following visual rating scale:
9. No damage to pinhole lesions present on whorl leaves.
8. Pinholes and small circular lesions present on whorl leaves.
7. Small circular lesions and a few small elongated (rectangular shaped) lesions up to 0.5" in length present on whorl and furl leaves.
6. Several small elongated lesions 0.5" to 1" in length on a few whorl and furl leaves.
5. Several large elongated lesions greater than 1" in length present on a few whorl and furl leaves and/or a few small to mid-sized uniform to irregular shaped holes (basement membrane consumed) in whorl and furl leaves.
4. Several large elongated lesions present on several whorl and furl leaves and/or several large uniform to irregular shaped holes in whorl and furl leaves.
3. Many elongated lesions of all sizes present on several whorl leaves plus several large uniform to irregular shaped holes in whorl and furl leaves.
2. Many elongated lesions of all sizes present on most whorl and furl leaves plus many mid to large-sized uniform to irregular shaped holes in whorl and furl leaves.
1. Whorl and furl leaves almost totally destroyed.

[b]Within a location, means with the same letter are not significantly different (Fisher's Protected LSD test, P > 0.05).

Figure 4:
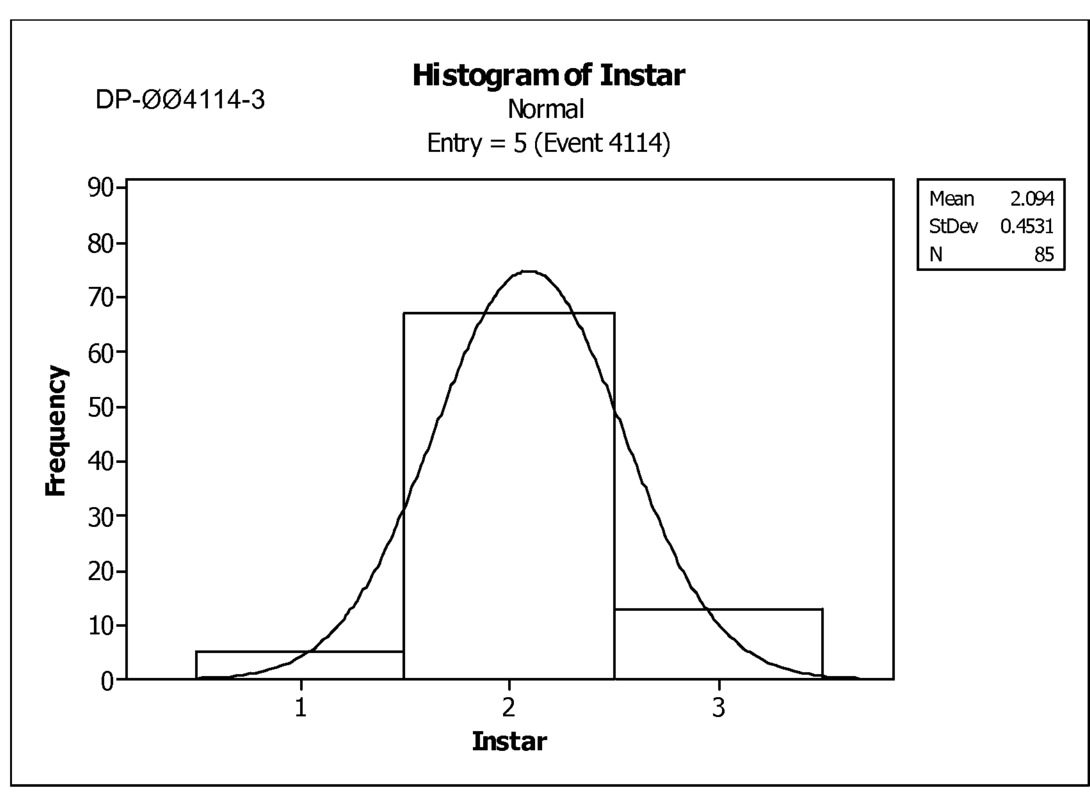
FIG. 4. Western corn rootworm (WCRW) larvae developmental effects in the sub-lethal seedling assay employing maize hybrid seedlings in the same genetic background: DP-004114-3 maize with an isoline as a negative control. Results are based on three replicates. Graphic profiles show the percent of larvae in each of three instars at 17 days post egg hatch. A shift towards instar 3 indicates a decrease in efficacy.
Figure 4:
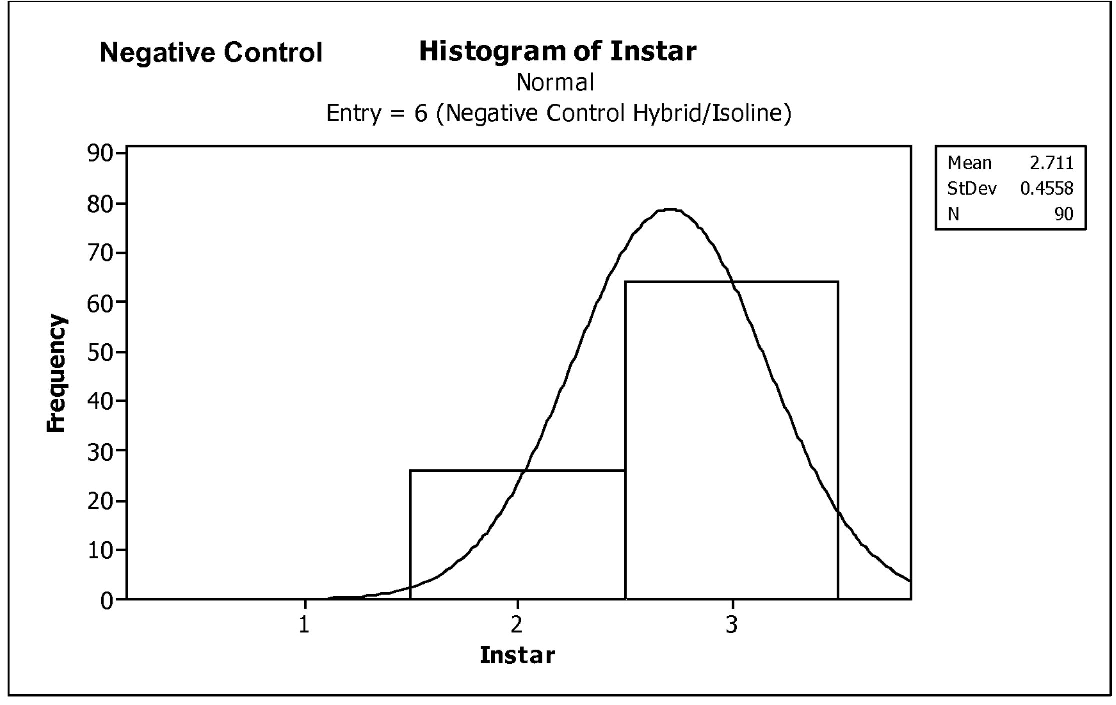

In addition to field efficacy studies, 4114 maize was evaluated in the lab-based sub-lethal seedling assay (SSA) (U.S. Publication No. 2006/0104904 the contents of which is hereby incorporated by reference). The SSA allowed for a comparison of the efficacy of 4114 maize to an unprotected control (near isoline) without the confounding effects of the field environment. The SSA technique involves exposing a population of neonate WCRW to maize seedlings containing either one of the 4114 maize events or non-transgenic (negative control) maize seedlings. Larvae were exposed for a period of 17 days from the date of initial egg hatch. The experimental unit for the SSA was a single plastic container with dimensions of 23×30×10 cm (Pactiv Corp., Lake Forest, IL). Entries were arranged in a randomized complete block with 3 replications per entry. For each entry, SSA setup involved placing 115 kernels into each container with 225 mL of a 1% thiophanate-methyl fungicide solution and 1000 mL of Metro-Mix 200 plant growth media (Scotts-Sierra Horticultural Products Company, Marysville, OH). Immediately after adding the Metro-Mix, WCRW eggs were infested onto the surface of each container at a rate of 1,000 eggs per container. WCRW eggs were pre-incubated at 25° C. so that initial egg hatch was timed to occur 5-7 days after container setup. Infested containers were held in a walk-in environmental chamber with settings of 25° C., 65% relative humidity, and 14:10 light:dark cycle. Larvae were extracted from the containers 17 days post-egg hatch using a Burlese funnel system. A random subsample of 30 larvae per container were selected and their head capsules measured under a dissecting microscope to categorize each into 1 of 3 instars. Data collected includes the age structure of the larval population determined from the number of larvae in each of three potential instars. Histograms that graphically displayed the age distribution of larvae for each entry were plotted and visually compared as shown in FIG. 4.

The pest spectrum for 4114 maize is provided in Table 13.

TABLE 13

Insect Pests That Are Controlled or Suppressed by DP-004114-3 Maize Expressing Cry1F, Cry34Ab1, and Cry35Ab1

| Scientific Name | Common Name | Insect Order |
|---|---|---|
| *Ostrinia nubilalis* | European corn borer (ECB) | Lepidoptera |
| *Helicoverpa zea* | Corn earworm (CEW) | Lepidoptera |
| *Spodoptera frugiperda* | Fall armyworm (FAW) | Lepidoptera |
| *Diatraea grandiosella* | Southwestern corn borer (SWCB) | Lepidoptera |
| *Richia albicosta* | Western bean cutworm (WBCW) | Lepidoptera |
| *Agrotis ipsilon* | Black cutworm (BCW) | Lepidoptera |
| *Elasmopalpus lignosellus* | Lesser corn stalk borer (LCSB) | Lepidoptera |
| *Diatrea crambidoides* | Southern corn stalk borer (SCSB) | Lepidoptera |
| *Diabrotica virgifera virgifera* | Western corn rootworm (WCRW) | Coleoptera |
| *Diabrotica virgifera zeae* | Mexican corn rootworm (MCR) | Coleoptera |
| *Diabrotica berberi* | Northern corn rootworm (NCR) | Coleoptera |
| *Diatrea saccharalis* | Sugarcane borer (SCB) | Coleoptera |

Example 6. Protein Expression and Concentration

Generation of Plant Material 4114 maize from the PHNAR×BC3F3 generation was grown in five locations in the United States and Canada. Each site employed a randomized complete block design containing four blocks, with each block separated by a buffer distance of at least 36 inches (0.9 m). Each entry was planted in 2-row plots bordered on each side by 1 row of border seed.

Leaf Tissue Collection and Processing

One leaf tissue sample was collected in each block at the V9 stage. All samples were collected from impartially selected, healthy, representative plants for each event. Each leaf sample was obtained by selecting the youngest leaf that had emerged at least 8 inches (20 cm, visible tissue) from the whorl. If this leaf was damaged or otherwise unhealthy, the next leaf below it was sampled. The leaf was pruned (cut) from the plant approximately 8 inches (20 cm) from the leaf tip. The leaf sample (including midrib) was cut into ≤1 inch (2.5 cm) pieces and placed in a 50-ml sample vial. The samples were then placed on dry ice until transferred to a freezer (≤−10° C.). Samples were shipped frozen and stored at ≤−10° C. upon arrival. All tissue samples were lyophilized, under vacuum, until dry. The lyophilized leaf samples were finely homogenized in preparation for analysis. Samples were stored frozen between processing steps.

Protein Concentration Determinations

Concentrations of the Cry1F, Cry34Ab1, Cry35Ab1, and PAT proteins were determined using specific quantitative ELISA methods.

Protein Extraction

Aliquots of processed leaf tissue samples were weighed into 1.2 mL tubes at the target weight of 10 mg. Each sample analyzed for Cry1F, Cry34Ab1, Cry35Ab1, and PAT protein concentrations was extracted in 0.6 mL of chilled PBST (Phosphate Buffered Saline plus Tween-20). Following centrifugation, supernatants were removed, diluted, and analyzed.

Determination of Cry1F, Cry34Ab1 and PAT Protein Concentration

The Cry1F, Cry34Ab1 and PAT ELISA kits employed were obtained from EnviroLogix, Inc. (Portland, ME), and the Cry35Ab1 ELISA kit employed was obtained from Acadia BioScience, LLC (Portland, ME). The ELISA method for each of these four proteins utilized a sequential "sandwich" format to determine the concentration of the protein in sample extracts. Standards (analyzed in triplicate wells) and diluted sample extracts (analyzed in duplicate wells) were incubated in plate pre-coated with an antibody specific to a single protein chosen from Cry1F, Cry34Ab1, Cry35Ab1 or PAT. Following incubation, unbound substances were washed from the plate. A different specific antibody for the respective selected protein, conjugated to the enzyme horseradish peroxidase (HRP), was added to the plate and incubated. Then, unbound substances were washed from the plate leaving the bound protein "sandwiched" between the antibody coated on the plate and the antibody-HRP conjugate. Detection of the bound antibody-protein complex was accomplished by the addition of substrate, which generated a colored product in the presence of HRP. The reaction was stopped with an acid solution and the optical density (OD) of each well was determined using plate reader. An average of the results from duplicate wells was used to determine the concentration of the Cry1F, Cry34Ab1, Cry35Ab1 or PAT protein in ng/mg sample dry weight.

Calculations for Determining Protein Concentrations

SoftMax® Pro software was used to perform the calculations required to convert the OD values obtained by the plate reader to protein concentrations.

1. Standard Curve

A standard curve was included on each ELISA plate. The equation for the standard curve was generated by the software, which used a quadratic fit to relate the mean OD values obtained for the standards to the respective standard concentration (ng/mL). The quadratic regression equation was applied as follows:

$$y=Cx^2+Bx+A$$

where x=known standard concentration and y=respective mean absorbance value (OD).

2. Sample Concentration

Interpolation of the sample concentration (ng/ml) was accomplished by solving for x in the above equation using values for A, B, and C determined by the standard curve.

$$\text{Sample Concentration (ng/mL)} = \frac{-B + \sqrt{B^2 - 4C(A - sampleOD)}}{2C}$$

e.g. Curve Parameters: A=0.0476, B=0.4556, C=−0.01910, and sample OD=1.438

$$\text{Sample Concentration} = \frac{-0.4556 + \sqrt{0.4556^2 - 4(-0.01910)(0.0476 - 1.488)}}{2(-0.01910)} = 3.6\ \text{ng/mL}$$

Sample concentration values were adjusted for the dilution factor expressed as 1: N Adjusted Concentration=Sample Concentration×Dilution Factor e.g. Sample Concentration=3.6 ng/mL and Dilution Factor=1:10

Adjusted Concentration=3.6 ng/mL×10=36 ng/mL

Adjusted sample concentration values were converted from ng/mL to ng/mg sample weight as follows:

ng/mg Sample Weight=ng/mL×Extraction Volume (mL)/Sample Weight (mg)

e.g. Concentration=36 ng/mL, Extraction Volume=0.60 ml, and

Sample Weight=10.0 mg ng/mg Sample Weight=36 ng/mg x 0.60 mL/10.0 mg=2.2 ng/mg

3. Lower Limit of Quantitation (LLOQ)

The LLOQ, in ng/mg sample weight, was calculated as follows:

$$LLOQ = \frac{\text{Reportable Assay } LLOQ \times \text{Extraction Volume}}{\text{Sample Target Weight}}$$

e.g. for PAT in leaf: reportable assay LLOQ=2.3 ng/mL, extraction volume=0.6 mL, and sample target weight=10 mg $$LLOQ = \frac{2.3\ \text{ng/mL} \times 0.6\ \text{mL}}{10\ \text{mg}} = 0.14\ \text{ng/mg sample weight}$$

Results

The proteins Cry1F, Cry34Ab1, Cry35Ab1, and PAT were detected in V9 leaf tissue of 4114 maize at the concentrations set forth in Table 14 below.

TABLE 14

Protein Concentrations in 4114 Maize

| | Protein concentration in ng/mg dry weight* | | | |
|---|---|---|---|---|
| | Cry1F | Cry34Ab1 | Cry35Ab1 | PAT |
| Mean ± SD | 9.7 ± 2.5 | 26 ± 3.1 | 33 ± 3.1 | 9.8 ± 3.3 |
| Range | 5.3-14 | 22-31 | 28-39 | 4.8-15 |

*The LLOQ for Cry1F and PAT was 0.14 ng/mg Dry Weight; the LLOQ for Cry34Ab1 and Cry35Ab1 were 0.16 ng/mg Dry Weight

Example 7: An Event-Specific Identification System for DP-004114-3 Maize

The event-specific system for DP-004114-3 maize was designed at the 5' junction between the DP-004114-3 insert and maize genomic region. The forward primer (08-O-2677, SEQ ID NO: 29) is situated within maize genomic DNA, the reverse primer (08-O-2678, SEQ ID NO: 30) is situated within the inserted DNA, and the binding site of the probe (08-QP74, SEQ ID NO: 31) spans the transition between DP-004114-3 insert and maize genomic DNA (Table 15). The optimum primer and probe concentrations were selected based on PCR efficiency and the ability to quantitate at the low (0.08% GM) and high (5% GM) ends of the dynamic range (Table 16).

TABLE 15

Primers and probe for DP-004114-3 event-specific PCR system

| Name | Sequence | SEQ ID NO. |
|---|---|---|
| 08-O-2677 | 5'-CGT TTG TAG CAC TTG CAC GTA GT-3' | 29 |
| 08-O-2678 | 5'-GGT AAC CGC TCT TCC AGT TGA A-3' | 30 |
| 08-QP74 (probe) | 5'-AAG CTT CAA CAC AGA TC-3' | 31 |

DP-004114-3 amplicon sequence (underlined are the primer and probe binding sites):

Length: 90 bp

CGTTTGTAGCACTTGCACGTAGTTACCCGGACCGAAGCTTCAACA
CAGATCTGATAGTTTAAACGCTCTTCAACTGGAAGAGCGGTTACC (SEQ ID NO: 32)

TABLE 16

Mastermix for DP-004114-3 event-specific PCR system

| Chemicals | Concentration | Final Concentration† | µl/reaction |
|---|---|---|---|
| Applied Biosystems TaqMan Universal PCR Master Mix, No AmpErase UNG | 2× | 1× | 10.0 |
| 08-0-2677 | 10 µM | 500 nM | 1.0 |
| 08-0-2678 | 10 µM | 900 nM | 1.8 |
| 08-QP74 | 10 µM | 200 nM | 0.4 |
| Sterile water | | | 1.8 |
| Total volume | | | 15.0 |

†Total PCR reaction is 20 µl (15 µl mastermix and 5 µl genomic DNA template).

TABLE 17

| Reaction and cycling parameters | |
|---|---|
| Format: | 15 μl mastermix + 5 μl genomic DNA template = 20 μl per reaction |
| Equipment: | Applied Biosystems ViiA7 real time thermal cycler |
| Software: | ViiA 7 RUO software version 1.1 |
| Plasticware: | MicroAmp ® Optical 96-well Reaction Plates (Applied Biosystems, Inc.); PRISM ™ 384-well Clear Optical Reaction Plates (Applied Biosystems, Inc.); and MicroAmp ™ Optical Adhesive Film (Applied Biosystems, Inc.) |

TABLE 18

Cycling parameters

| Step | Stage | Temp. | Time | Data collection | Cycles |
|---|---|---|---|---|---|
| 1 | Initial enzyme activation | 95° C. | 600 s | no | 1× |
| 2 | Amplification Denaturation | 95° C. | 15 s | no | 40× |
| 3 | Annealing & Extension | 60° C. | 60 s | Yes | |

The assay format used a standard curve having four standard points, each in triplicate. The standards were produced by preparing a solution of 40 ng/μl of total genomic maize DNA with 10% DP-004114-3 maize DNA followed by serial dilutions in 0.1×TE buffer containing 10 ng/μl salmon sperm DNA. Negative controls (NTC) were measured in triplicate for each system to verify purity of the reagents. Each sample (unknown) was analyzed at 200 ng genomic maize DNA per reaction in triplicates (six reactions per sample in total for both PCR systems). The relative content of DP-004114-3 maize to total maize DNA was subsequently calculated by determining the mean of the copy numbers based on the standard curves (linear regression of threshold cycle ($C_T$) value versus log [copy number]) and calculating the ratios of DP-004114-3 maize copy number/total copy number of haploid maize genomes.

This event-specific quantitative PCR system for detection of DP-004114-3 maize DNA was developed, optimized, and validated on Applied Biosystem's ViiA 7™ real-time PCR system. The method can also be applied on a different platform however, with minimal optimization and adaptation.

The event-specific real-time PCR method described here can be applied to determine the relative content of DP-004114-3 maize DNA in total genomic maize DNA. The method performs in a linear manner with an acceptable level of accuracy and precision over the whole range from 0.08% to 5.0% DP-004114-3 content. The method was developed and validated with genomic DNA extracted from maize seeds. However, the assay can be applied to any matrix from which genomic DNA with sufficient quantity and quality can be purified.

Example 8: Gel-Based PCR Detection Method for the Maize Event DP-004114-3

This protocol describes a qualitative gel-based PCR assay to detect the presence of DP-004114-3 maize DNA. The PCR detection method is used in conjunction with a DNA extraction method which yields DNA of sufficient quality and quantity.

A PCR system for DP-004114-3 maize was developed using primers to amplify the 5' border junction between maize genomic DNA and the DP-004114-3 insert. The forward primer is located in the maize genomic region, and the reverse primer is located in the transgene insert.

```
Forward Primer (11-O-4127) (SEQ ID NO: 33); 5'- GGA CCC TGT TCA CAA CAC AGG GCT
C-3'
Reverse Primer (11-O-4128) (SEQ ID NO: 34): 5'- GGC CGA AGC TTC GGT CCG G-3'
Amplicon Sequence (underlined are the primer bindinq sites) (SEQ ID NO: 35):
ggaccctgttcacaacacagggctctggctttggagcctctcgtttgtagcacttgcacgtagttacccggaccgaagcttcaacac
agatctgatagtttaaacgctcttcaactggaagagcggttacccggaccgaagcttcggcc
```

Equipment and Materials Used:

| Equipment/Plasticware | Specification |
|---|---|
| 96-well GeneAmp PCR System 9700 | Applied Biosystems, Foster City, Ca; or equivalent |
| Gel Electrophoresis Unit | Sub Cell GT, Bio-Rad, Hercules, CA; or equivalent |
| Power supply | Power Pac, Bio-Rad, Hercules, CA; or equivalent |
| Gel documentation | Bio-Rad Molecular Imager Gel Doc XR+ Imager System; or equivalent |
| | Quantity One, 2.0 Software; or equivalent |
| Pipettes with adjustable volume | Ranin, Woburn, MA; Research: 0.5-10 μl; 2-20 μl, 20-200 μl, 100-1000 μl; or equivalent |
| Filter Tips | Appropriate for the pipette models used |
| PCR Reaction tubes and Caps | Applied Biosystems, Foster City, CA; or equivalent |
| Reaction tubes 1.5 ml | Eppendorf, Hamburg, Germany; or equivalent |

Reagents, Buffers and Solutions:

| Reagent | Specification |
|---|---|
| 2× Promega PCR Master Mix (contains 15 mM $MgCl_2$ and Taq polymerase) | Promega, Madison, WI; or equivalent |
| PCR Marker | Promega, Madison, WI; or equivalent |
| UltraPure Agarose | Invitrogen, Carlsbad, CA; or equivalent |
| Ethidium bromide | EMD, Darmstadt, Germany; or equivalent |
| 6× Promega Blue Orange Loading dye | Promega, Madison, WI; or equivalent |
| 10× TBE buffer | Mediatech, Herndon, VA; or equivalent |
| Molecular Grade Water | Mediatech, Herndon, VA; or equivalent |

Procedures

Reagents were thoroughly mixed before use. A reaction mix consisting of all components of the PCR reaction were prepared, except template DNA, in sufficient quantity for all reactions to be performed. Reagents and the master mix were kept on ice.

Preparation of the Mastermix for the PCR System:

| Component | Concentration | Final concentration | µl/rxn |
|---|---|---|---|
| Promega 2× PCR buffer | 2× | 1× | 12.50 |
| Forward Primer (11-O-4127) | 10 µM | 200 nM | 0.50 |
| Reverse Primer (11-O-4128) | 10 µM | 200 nM | 0.50 |
| Sterile water | | | 6.50 |
| Total volume | | | 20.00 |

Components were mixed and 20 µl of the thoroughly mixed mastermix dispensed into reaction tubes. 5 µl of a 20 ng/µl template genomic DNA were added.

No Template Controls: Instead of genomic DNA, 5 µl of the diluent used for diluting the test DNA samples were added to their proper concentration; e.g. water, 0.1× TE, etc.

Positive controls: 5 µl of e.g. 1% DP-004114-3 (20 ng/µl) maize DNA were added.

After addition of template to mastermix, reaction tubes were capped and immediately placed in pre-heated PCR machine and run was initiated.

Cycling Parameters

The PCR assay was performed using an Applied Biosystems' 96-well GeneAmp PCR System 9700 with the ramp speed set to 'GeneAmp 9600'. The cycling parameters were as follows:

PCR Profile for DP-004114-3 Detection Method

| Step | Cycle element | | T (° C.) | Time (min:sec) | Cycles |
|---|---|---|---|---|---|
| 1 | Initial Denaturation | | 95 | 2:00 | 1× |
| 2 | Amplification | Denaturation | 95 | 00:30 | |
| 3 | | Annealing | 66 | 00:30 | 35× |
| 4 | | Extension | 72 | 00:30 | |
| 5 | Final Extension | | 72 | 07:00 | 1× |

Gel Electrophoresis

PCR products were mixed with enough 6× loading buffer added for a final concentration of 1× loading buffer (example: 25 µl PCR product plus 5 µl 6× loading buffer). 15 µl PCR products/loading dye mixture were loaded on a 2.5% agarose/1×TBE gel. Gel was run with a maximum of 7 V per cm (measured electrode to electrode) until the fragments were separated properly. Gel was run long enough to get clear separation of marker bands in the 50 to 200 bp range. The agarose gel was stained in an ethidium bromide bath (1.5 µg per ml in distilled water or buffer) for approximately 15 min, rinsed with distilled water or 1×TBE, and photographed under UV-light with an appropriate gel-documentation system. The PCR product for DP-004114-3 maize was 149 bp in length.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A method of detecting the presence of a nucleic acid molecule comprising corn event DP-004114-3 in a biological sample comprising corn nucleic acids, comprising:

(a) contacting said sample with a primer pair, wherein the primer pair is either SEQ ID NO: 29-30 or SEQ ID NO: 33-34, that when used in a nucleic acid amplification reaction comprising corn event DP-004114-3 DNA, produces an amplicon that is diagnostic for corn event DP-004114-3, (b) performing a nucleic acid amplification reaction; and (c) detecting the amplicon so produced.

* * * * *

SEQUENCE LISTING

```
Sequence total quantity: 35
SEQ ID NO: 1            moltype = AA  length = 605
FEATURE                 Location/Qualifiers
REGION                  1..605
                        note = Cry1F
source                  1..605
                        mol_type = protein
                        organism = Bacillus thuringiensis
SEQUENCE: 1
MENNIQNQCV PYNCLNNPEV EILNEERSTG RLPLDISLSL TRFLLSEFVP GVGVAFGLFD  60
LIWGFITPSD WSLFLLQIEQ LIEQRIETLE RNRAITTLRG LADSYEIYIE ALREWEANPN  120
NAQLREDVRI RFANTDDALI TAINNFTLTS FEIPLLSVYV QAANLHLSLL RDAVSFGQGW  180
GLDIATVNNH YNRLINLIHR YTKHCLDTYN QGLENLRGTN TRQWARFNQF RRDLTLTVLD  240
IVALFPNYDV RTYPIQTSSQ LTREIYTSSV IEDSPVSANI PNGFNRAEFG VRPPHLMDFM  300
NSLFVTAETV RSQTVWGGHL VSSRNTAGNR INFPSYGVFN PGGAIWIADE DPRPFYRTLS  360
DPVFVRGGFG NPHYVLGLRG VAFQQTGTNH TRTFRNSGTI DSLDEIPPQD NSGAPWNDYS  420
HVLNHVTFVR WPGEISGSDS WRAPMFSWTH RSATPTNTID PERITQIPLV KAHTLQSGTT  480
VVRGPGFTGG DILRRTSGGP FAYTIVNING QLPQRYRARI RYASTTNLRI YVTVAGERIF  540
```

```
AGQFNKTMDT GDPLTFQSFS YATINTAFTF PMSQSSFTVG ADTFSSGNEV YIDRFELIPV  600
TATLE                                                              605

SEQ ID NO: 2           moltype = AA  length = 123
FEATURE                Location/Qualifiers
REGION                 1..123
                       note = Cry34Ab1
source                 1..123
                       mol_type = protein
                       organism = Bacillus thuringiensis
SEQUENCE: 2
MSAREVHIDV NNKTGHTLQL EDKTKLDGGR WRTSPTNVAN DQIKTFVAES NGFMTGTEGT  60
IYYSINGEAE ISLYFDNPFA GSNKYDGHSN KSQYEIITQG GSGNQSHVTY TIQTTSSRYG  120
HKS                                                                123

SEQ ID NO: 3           moltype = AA  length = 383
FEATURE                Location/Qualifiers
REGION                 1..383
                       note = Cry35Ab1
source                 1..383
                       mol_type = protein
                       organism = Bacillus thuringiensis
SEQUENCE: 3
MLDTNKVYEI SNHANGLYAA TYLSLDDSGV SLMNKNDDDI DDYNLKWFLF PIDDDQYIIT  60
SYAANNCKVW NVNNDKINVS TYSSTNSIQK WQIKANGSSY VIQSDNGKVL TAGTGQALGL  120
IRLTDESSNN PNQQWNLTSV QTIQLPQKPI IDTKLKDYPK YSPTGNIDNG TSPQLMGWTL  180
VPCIMVNDPN IDKNTQIKTT PYYILKKYQY WQRAVGSNVA LRPHEKKSYT YEWGTEIDQK  240
TTIINTLGFQ INIDSGMKFD IPEVGGTDE IKTQLNEELK IEYSHETKIM EKYQEQSEID  300
NPTDQSMNSI GFLTITSLEL YRYNGSEIRI MQIQTSDNDT YNVTSYPNHQ QALLLLTNHS  360
YEEVEEITNI PKSTLKKLKK YYF                                          383

SEQ ID NO: 4           moltype = AA  length = 183
FEATURE                Location/Qualifiers
REGION                 1..183
                       note = Phosphinothricin acetyl transferase protein
source                 1..183
                       mol_type = protein
                       organism = Streptomyces viridochromogenes
SEQUENCE: 4
MSPERRPVEI RPATAADMAA VCDIVNHYIE TSTVNFRTEP QTPQEWIDDL ERLQDRYPWL  60
VAEVEGVVAG IAYAGPWKAR NAYDWTVEST VYVSHRHQRL GLGSTLYTHL LKSMEAQGFK  120
SVVAVIGLPN DPSVRLHEAL GYTARGTLRA AGYKHGGWHD VGFWQRDFEL PAPPRPVRPV  180
TQI                                                                183

SEQ ID NO: 5           moltype = DNA  length = 11978
FEATURE                Location/Qualifiers
misc_feature           1..11978
                       note = Complete sequence of the T-DNA region of Plasmid
                        PHP27118
source                 1..11978
                       mol_type = other DNA
                       organism = synthetic construct
SEQUENCE: 5
gtttacccgc caatatatcc tgtcaaacac tgatagttta aacgctcttc aactggaaga  60
gcggttaccc ggaccgaagc ttcggccggg gcccatcgat atccgcgggc atgcctgcag  120
tgcagcgtga cccggtcgtg cccctctcta gagataatga gcattgcatg tctaagttat  180
aaaaaattac cacatatttt ttttgtcaca cttgtttgaa gtgcagttta tctatcttta  240
tacatatatt taaactttac tctacgaata atataatcta tagtactaca ataatatcag  300
tgttttagag aatcatataa atgaacagtt agacatggtc taaaggacaa ttgagtattt  360
tgacaacagg actctacagt tttatctttt tagtgtgcat gtgttctcct ttttttttgc  420
aaatagcttc acctatataa tacttcatcc attttattag tacatccatt tagggtttag  480
ggttaatggt ttttatagac taattttttt agtacatcta ttttattcta ttttagcctc  540
taaattaaga aaactaaaac tctattttag tttttttatt taataattta gatataaaat  600
agaataaaat aaagtgacta aaaattaaac aaataccctt taagaaatta aaaaaactaa  660
ggaaacattt ttcttgtttc gagtagataa tgccagcctg ttaaacgccg tcgacgagtc  720
taacggacac caaccagcga accagcagcg tcgcgtcggg ccaagcgaag cagacggcac  780
ggcatctctg tcgctgcctc tggacccctc tcgagagttc cgctccaccg ttggacttgc  840
tccgctgtcg gcatccagaa attgcgtggc ggagcggcag acgtgagccg gcacggcagg  900
cggcctcctc ctcctctcac ggcaccggca gctacggggg attcctttcc caccgctcct  960
tcgctttccc ttcctcgccc gccgtaataa atagacaccc cctccacacc ctctttcccc  1020
aacctcgtgt tgttcggagc gcacacacac acaaccagat ctcccccaaa tccacccgtc  1080
ggcacctccg cttcaaggta cgccgctcgt cctccccccc ccccctctc tacttctct  1140
agatcggcgt tccggtccat ggttagggcc cggtagttct acttctgttc atgtttgtgt  1200
tagatccgtg tttgtgttag atccgtgctg ctagcgttcg tacacggatg cgacctgtac  1260
gtcagacacg ttctgattgc taacttgcca gtgtttctct ttggggaatc ctgggatggc  1320
tctagccgtt ccgcagacgg gatcgatttc atgatttttt ttgtttcgtt gcatagggtt  1380
tggtttgccc ttttccttta tttcaatata tgccgtgcac ttgtttgtcg ggtcatcttt  1440
tcatgctttt ttttgtcttg gttgtgatga tgtggtctgg ttgggcggtc gttctagatc  1500
ggagtagaat tctgtttcaa actacctggt ggatttatta attttggatc tgtatgtgtg  1560
```

-continued

```
tgccatacat attcatagtt acgaattgaa gatgatggat ggaaatatcg atctaggata  1620
ggtatacatg ttgatgcggg ttttactgat gcatatacag agatgctttt tgttcgcttg  1680
gttgtgatga tgtggtgtgg ttgggcggtc gttcattcgt tctagatcgg agtagaatac  1740
tgtttcaaac tacctggtgt atttattaat tttggaactg tatgtgtgtg tcatacatct  1800
tcatagttac gagtttaaga tggatggaaa tatcgatcta ggataggtat acatgttgat  1860
gtgggtttta ctgatgcata tacatgatgg catatgcagc atctattcat atgctctaac  1920
cttgagtacc tatctattat aataaacaag tatgttttat aattattttg atcttgatat  1980
acttggatga tggcatatgc agcagctata tgtggatttt tttagccctg ccttcatacg  2040
ctatttattt gcttggtact gtttcttttg tcgatgctca ccctgttgtt tggtgttact  2100
tctgcaggtc gactctagag gatccaacaa tggagaacaa catacagaat cagtgcgtcc  2160
cctacaactg cctcaacaat cctgaagtag agattctcaa cgaagagagg tcgactggca  2220
gattgccgtt agacatctcc ctgtccctta cacgtttcct gttgtctgag tttgttccag  2280
gtgtgggagt tgcgtttggc ctcttcgacc tcatctgggg cttcatcact ccatctgatt  2340
ggagcctctt tcttctccag attgaacagt tgattgaaca aaggattgag accttggaaa  2400
ggaatcgggc catcactacc cttcgtggct tagcagacag ctatgagatc tacattgaag  2460
cactaagaga gtgggaagcc aatcctaaca atgcccaact gagagaagat gtgcgtatac  2520
gctttgctaa cacagatgat gctttgatca cagccatcaa caacttcacc cttaccagct  2580
tcgagatccc tcttctctcg gtctatgttc aagctgctaa cctgcacttg tcactactgc  2640
gcgacgctgt gtcgtttggg caaggttggg gactggacat agctactgtc aacaatcact  2700
acaacagact catcaatctg attcatcgat acacgaaaca ttgtttggat acctacaatc  2760
agggattgga gaacctgaga ggtactaaca ctcgccaatg ggccaggttc aatcagttca  2820
ggagagacct tacacttact gtgttagaca tagttgctct ctttccgaac tacgatgttc  2880
gtacctatcc gattcaaacg tcatcccaac ttacaaggga gatctacacc agttcagtca  2940
ttgaagactc tccagtttct gcgaacatac ccaatggttt caacagggct gagtttggag  3000
tcagaccacc ccatctcatg gacttcatga actctttgtt tgtgactgca gagactgtta  3060
gatcccaaac tgtgtgggga ggacacttag ttagctcacg caacacggct ggcaatcgta  3120
tcaactttcc tagttacggg gtcttcaatc ccgggggcgc catctggatt gcagatgaag  3180
atccacgtcc tttctatcgg accttgtcag atcctgtctt cgtccgagga ggctttggca  3240
atcctcacta tgtactcggt cttaggggag tggcctttca acaaactggt acgaatcaca  3300
cccgcacatt caggaactcc gggaccattg actctctaga tgagatacca cctcaagaca  3360
acagcggcgc accttggaat gactactccc atgtgctgaa tcatgttacc tttgtgcgct  3420
ggccaggtga gatctcaggt tccgactcat ggagagcacc aatgttctct tggacgcatc  3480
gtagcgctac ccccacaaac accattgatc cagagagaat cactcagatt cccttggtga  3540
aggcacacac acttcagtca ggaactacag ttgtaagagg gccggggttc acgggaggag  3600
acattcttcg acgcactagt ggaggaccat tcgcgtacac cattgtcaac atcaatgggc  3660
aacttcccca aaggtatcgt gccaggatac gctatgcctc tactaccaat ctaagaatct  3720
acgttacggt tgcaggtgaa cggatctttg ctggtcagtt caacaagaca atggataccg  3780
gtgatccact tacattccaa tctttctcct acgccactat caacaccgcg ttcacctttc  3840
caatgagcca gagcagtttc acagtaggtg ctgatacctt cagttcaggc aacgaagtgt  3900
acattgacag gtttgagttg attccagtta ctgccacact cgagtaagga tccgtcgacc  3960
tgcagccaag ctttcgcgag ctcgagatcc ccgacatatg ccccggtttc gttgcgacta  4020
acatgagttc ttggacaaat ttgattggac ctgatgagat gatccaaccc gaggatatag  4080
caaagctcgt tcgtgcagca atggaacggc caaaccgtgc ttttgtcccc aagaatgagg  4140
tgctatgcat gaaggaatct acccgttgat gtccaacagt ctcagggtta atgtctatgt  4200
atcttaaata atgttgtcgg tattttgtaa tctcatatag attttcactg tgcgacgcaa  4260
aaatattaaa taaatattat tattatctac gttttgattg agatatcatc aatattataa  4320
taaaaatatc cattaaacac gatttgatac aaatgacagt caataatctg atttgaatat  4380
ttattaattg taacgaatta cataaagatc gaatagaaaa tactgcactg caaatgaaaa  4440
ttaacacata ctaataaatg cgtcaaatat ctttgccaag atcaagcgga gtgagggcct  4500
catatccggt ctcagttaca agcacggtat ccccgaagcg cgctccacca atgccctcga  4560
catagatgcc gggctcgacg ctgaggacat tgcctacctt gagcatggtc tcagcgccgg  4620
ctttaagctc aatcccatcc caatctgaat atcctatccc gcgcccagtc cggtgtaaga  4680
acgggtctgt ccatccacct ctgttgggaa ttccggtccg ggtcaccttt gtccaccaag  4740
atggaactgc ggccagcttg catgcctgca gtgcagcgtg acccggtcgt gcccctctct  4800
agagataatg agcattgcat gtctaagtta taaaaaatta ccacatattt tttttgtcac  4860
acttgtttga agtgcagttt atctatcttt atacatatat ttaaacttta ctctacgaat  4920
aatataatct atagtactac aataatatca gtgttttaga gaatcatata aatgaacagt  4980
tagacatggt ctaaaggaca attgagtatt ttgacaacag gactctacag ttttatcttt  5040
ttagtgtgca tgtgttctcc tttttttttg caaatagctt cacctatata atacttcatc  5100
cattttatta gtacatccat ttagggttta gggttaatgg tttttataga ctaatttttt  5160
tagtacatct attttattct attttagcct ctaaattaag aaaactaaaa ctctatttta  5220
gtttttttat ttaataattt agatataaaa tagaataaaa taaagtgact aaaaattaaa  5280
caaataccct ttaagaaatt aaaaaaacta aggaaacatt tttcttgttt cgagtagata  5340
atgccagcct gttaaacgcc gtcgacgagt ctaacggaca ccaaccagcg aaccagcagc  5400
gtcgcgtcgg gccaagcgaa gcagacggca cggcatctct gtcgctgcct ctggacccct  5460
ctcgagagtt ccgctccacc gttggacttg ctccgctgtc ggcatccaga aattgcgtgg  5520
cggagcggca gacgtgagcc ggcacggcag gcggcctcct cctcctctca cggcaccggc  5580
agctacgggg gattcctttc ccaccgctcc ttcgctttcc cttcctcgcc cgcccgtaata  5640
aatagacacc ccctccacac cctctttccc caacctcgtg ttgttcggag cgcacacaca  5700
cacaaccaga tctcccccaa atccacccgt cggcacctcc gcttcaaggt acgccgctcg  5760
tcctcccccc ccccccctct ctaccttctc tagatcggcg ttccggtcca tggttagggc  5820
ccggtagttc tacttctgtt catgtttgtg ttagatccgt gtttgtgtta gatccgtgct  5880
gctagcgttc gtacacggat gcgacctgta cgtcagacac gttctgattg ctaacttgcc  5940
agtgtttctc tttggggaat cctgggatgg ctctagccgt tccgcagacg ggatcgattt  6000
catgattttt tttgtttcgt tgcatagggt ttggtttgcc cttttccttt atttcaatat  6060
atgccgtgca cttgtttgtc gggtcatctt ttcatgcttt tttttgtctt ggttgtgatg  6120
atgtggtctg gttgggcggt cgttctagat cggagtagaa ttctgtttca aactacctgg  6180
tggatttatt aattttggat ctgtatgtgt gtgccataca tattcatagt tacgaattga  6240
agatgatgga tggaaatatc gatctaggat aggtatacat gttgatgcgg gttttactga  6300
```

-continued

```
tgcatataca gagatgcttt ttgttcgctt ggttgtgatg atgtggtgtg gttgggcggt  6360
cgttcattcg ttctagatcg gagtagaata ctgtttcaaa ctacctggtg tatttattaa  6420
ttttggaact gtatgtgtgt gtcatacatc ttcatagtta cgagtttaag atggatggaa  6480
atatcgatct aggataggta tacatgttga tgtgggtttt actgatgcat atacatgatg  6540
gcatatgcag catctattca tatgctctaa ccttgagtac ctatctatta taataaacaa  6600
gtatgtttta taattatttt gatcttgata tacttggatg atggcatatg cagcagctat  6660
atgtggattt ttttagccct gccttcatac gctatttatt tgcttggtac tgtttctttt  6720
gtcgatgctc accctgttgt ttggtgttac ttctgcaggt cgactctaga ggatccacac  6780
gacaccatgt ccgcccgcga ggtgcacatc gacgtgaaca acaagaccgg ccacaccctc  6840
cagctggagg acaagaccaa gctcgacggc ggcaggtggc gcacctcccc gaccaacgtg  6900
gccaacgacc agatcaagac cttcgtggcc gaatccaacg gcttcatgac cggcaccgag  6960
ggcaccatct actactcaat taatggcgag gccgagatca gcctctactt cgacaacccg  7020
ttcgccggct ccaacaaata cgacggccac tccaacaagt cccagtacga gatcatcacc  7080
cagggcggct ccggcaacca gtcccacgtg acctacacca tccagaccac ctcctcccgc  7140
tacggccaca agtcctgagt catgagtcat gagtcagtta acctagactt gtccatcttc  7200
tggattggcc aacttaatta atgtatgaaa taaaaggatg cacacatagt gacatgctaa  7260
tcactataat gtgggcatca aagttgtgtg ttatgtgtaa ttactagtta tctgaataaa  7320
agagaaagag atcatccata tttcttatcc taaatgaatg tcacgtgtct ttataattct  7380
ttgatgaacc agatgcattt cattaaccaa atccatatac atataaatat taatcatata  7440
taattaatat caattgggtt agcaaaacaa atctagtcta ggtgtgtttt gcgaatgcgg  7500
ccgcggaccg aattggggat ctgcatgaaa gaaactgtcg cactgctgaa ccgcaccttg  7560
tcactttcat cgaacacgac ctgtgcccaa gatgacggtg ctgcggtcta agtgaggctg  7620
aattgccttg gacagaagcg gactccctac aattagttag gccaaacggt gcatccatgt  7680
gtagctccgg gctcgggctg tatcgccatc tgcaatagca tccatggagc tcgttccatg  7740
tagttggaga tgaaccaatg atcgggcgtg tggacgtatg ttcctgtgta ctccgatagt  7800
agagtacgtg ttagctcttt catggtgcaa gtgaaatttg tgttggttta attaccccta  7860
cgttagttgc gggacaggag acacatcatg aatttaaagg cgatgatgtc ctctcctgta  7920
atgttattct tttgatgtga tgaatcaaaa tgtcatataa aacatttgtt gctctttagt  7980
taggcctgat cgtagaacga aatgctcgtg tagcggggct acgagcctat gacgcaataa  8040
cactggtttg ccggcccgga gtcgcttgac aaaaaaaagc atgttaagtt tatttacaat  8100
tcaaaaccta acatattata ttccctcaaa gcaggttcac gatcacacct gtacctaaaa  8160
aaaacatgaa gaatatatta ctccattatt atgagatgaa ccacttggca agagtggtaa  8220
gctatataaa aaaatgaaca ttattacgag atgttatatg ccattatatt gattcgaaga  8280
tatatgtttc tttctcccac gggcacctaa cggatacatg ataaggccaa ggcagatcac  8340
gggaaattat tcgaatacat gttacgccct attgccggaa aaaaaatgca gggcaggtgt  8400
tggccgtagc gatttaagca cttaagctgg aggttgccac acttggatgc aagcgtctga  8460
cccttctaaa aaatcggcgg ctttgtccgt atccgtatcc cctatccaac atctagctgg  8520
ccacacgacg gggctgggca gatcgtggat gccgggtcga cgtcgatcgt cagccatcat  8580
agaccaatcg accatctgtt atggatgctt gctagctaga ctagtcagac ataaaatttg  8640
gatactttct cccaactggg agacggggac tgatgtgcag ctgcacgtga gctaaatttt  8700
tccctataaa tatgcatgaa atactgcatt atcttgccac agccactgcc acagccagat  8760
aacaagtgca gctggtagca cgcaacgcat agctctggac ttgtagctag gtagccaacc  8820
ggatccacac gacaccatgc tcgacaccaa caaggtgtac gagatcagca accacgccaa  8880
cggcctctac gccgccacct acctctccct cgacgactcc ggcgtgtccc tcatgaacaa  8940
gaacgacgac gacatcgacg actacaacct caagtggttc ctcttcccga tcgacgacga  9000
ccagtacatc atcacctcct acgccgccaa caactgcaag gtgtggaacg tgaacaacga  9060
caagattaat gtgtcaacct actcctccac caactccatc cagaagtggc agatcaaggc  9120
caacggctcc tcctacgtga tccagtccga caacggcaag gtgctcaccg ccggcaccgg  9180
ccaggccctc ggcctcatcc gcctcaccga cgagtcctcc aacaacccga accagcaatg  9240
gaacctgacg tccgtgcaga ccatccagct cccgcagaag ccgatcatcg acaccaagct  9300
caaggactac ccgaagtact ccccgaccgg caacatcgac aacggcacct ccccgcagct  9360
catgggctgg accctcgtgc cgtgcatcat ggtgaacgac ccgaacatcg acaagaacac  9420
ccagatcaag accaccccgt actacatcct caagaagtac cagtactggc agagggccgt  9480
gggctccaac gtcgcgctcc gcccgcacga gaagaagtcc tacacctacg agtggggcac  9540
cgagatcgac cagaagacca ccatcatcaa caccctcggc ttccagatca acatcgacag  9600
cggcatgaag ttcgacatcc cggaggtggg cggcggtacc gacgagatca agacccagct  9660
caacgaggag ctcaagatcg agtattcaca tgagacgaag atcatggaga agtaccagga  9720
gcagtccgag atcgacaacc cgaccgacca gtccatgaac tccatcggct tcctcaccat  9780
cacctccctg gagctctacc gctacaacgg ctccgagatc cgcatcatgc agatccagac  9840
ctccgacaac gacacctaca acgtgacctc ctacccgaac caccagcagg ccctgctgct  9900
gctgaccaac cactcctacg aggaggtgga ggagatcacc aacatcccga agtccaccct  9960
caagaagctc aagaagtact acttctgagt catgagtcat gagtcagtta acctagactt  10020
gtccatcttc tggattggcc aacttaatta atgtatgaaa taaaaggatg cacacatagt  10080
gacatgctaa tcactataat gtgggcatca aagttgtgtg ttatgtgtaa ttactagtta  10140
tctgaataaa agagaaagag atcatccata tttcttatcc taaatgaatg tcacgtgtct  10200
ttataattct ttgatgaacc agatgcattt cattaaccaa atccatatac atataaatat  10260
taatcatata taattaatat caattgggtt agcaaaacaa atctagtcta ggtgtgtttt  10320
gcgaattatc gatgggcccc ggccgaagct ggccgcggac cgaattccca tggagtcaaa  10380
gattcaaata gaggacctaa cagaactcgc cgtaaagact ggcgaacagt tcatacagag  10440
tctcttacga ctcaatgaca agaagaaaat cttcgtcaac atggtggagc acgacacgct  10500
tgtctactcc aaaaatatca aagatacagt ctcagaagac caaagggcaa ttgagacttt  10560
tcaacaaagg gtaatatccg gaaacctcct cggattccat tgcccagcta tctgtcactt  10620
tattgtgaag atagtggaaa aggaaggtgg ctcctacaaa tgccatcatt gcgataaagg  10680
aaaggccatc gttgaagatg cctctgccga cagtggtccc aaagatggac ccccacccac  10740
gaggagcatc gtggaaaaag aagacgttcc aaccacgtct tcaaagcaag tggattgatg  10800
tgatatctcc actgacgtaa gggatgacgc acaatcccac tatccttcgc aagacccttc  10860
ctctatataa ggaagttcat ttcatttgga gaggacaggg tacccgggga tccaccatgt  10920
ctccggagag gagaccagtt gagattaggc cagctacagc agctgatatg gccgcggttt  10980
gtgatatcgt taaccattac attgagacgt ctacagtgaa ctttaggaca gagccacaaa  11040
```

```
caccacaaga gtggattgat gatctagaga ggttgcaaga tagataccct tggttggttg  11100
ctgaggttga gggtgttgtg gctggtattg cttacgctgg gccctggaag gctaggaacg  11160
cttacgattg gacagttgag agtactgttt acgtgtcaca taggcatcaa aggttgggcc  11220
taggatccac attgtacaca catttgctta agtctatgga ggcgcaaggt tttaagtctg  11280
tggttgctgt tataggcctt ccaaacgatc catctgttag gttgcatgag gctttgggat  11340
acacagcccg gggtacattg cgcgcagctg gatacaagca tggtggatgg catgatgttg  11400
gtttttggca aagggatttt gagttgccag ctcctccaag gccagttagg ccagttaccc  11460
agatctgagt cgacctgcag gcatgcccgc tgaaatcacc agtctctctc tacaaatcta  11520
tctctctcta taataatgtg tgagtagttc ccagataagg gaattagggt tcttataggg  11580
tttcgctcat gtgttgagca tataagaaac ccttagtatg tatttgtatt tgtaaaatac  11640
ttctatcaat aaaatttcta attcctaaaa ccaaaatcca gggcgagctc gaattcgagc  11700
tcgagcccgg gtggatcctc tagagtcgac ctgcagaagc ttcggtccgg cgcgcctcta  11760
gttgaagaca cgttcatgtc ttcatcgtaa gaagacactc agtagtcttc ggccagaatg  11820
gcctaactca aggccatcgt ggcctcttgc tcttcaggat gaagagctat gtttaaacgt  11880
gcaagcgcta ctagacaatt cagtacatta aaaacgtccg caatgtgtta ttaagttgtc  11940
taagcgtcaa tttgtttaca ccacaatata tcctgcca                          11978

SEQ ID NO: 6           moltype = DNA  length = 16752
FEATURE                Location/Qualifiers
misc_feature           1..16752
                       note = The complete sequence of the insert and flanking
                        regions of event DP-004114-3
source                 1..16752
                       mol_type = other DNA
                       organism = synthetic construct
SEQUENCE: 6
gagcatatcc agcaccagct ggtaccaagg tcgggtctct gtgctagtgc tattagctag  60
tgtaaggagc gagtaggtca gttaaggctg gtgcgtcgtg agggctgtct tgtgtgtagc  120
tacagcagac ggttcatcag aaggattatt cgtgcagtat atacagtaca actagacaat  180
gatgttgatg attggtctag agctagaggc ctatagccct atactactgt gtattgtccg  240
ccgttttagt tttttggtcc catcccatca atgcaaccgc cttgttttgc tccaattgtc  300
ccgttcctgc gcctcgcttt tgctctgtcg catcgcatac aaaaaaaaaa acgccgcgcc  360
ggctttgaat cgcgcccccc aactgctcca accaggcaac ggacacggcc accgtccgtg  420
tcgcgagcaa aaaaacaaaa agaggaacgc gtccaggacg aagcagtcca ctgccgctgt  480
ggccggcaaa agatctggtt gagcacatgg agattggaga aggttggttg gttcttctgg  540
aaacgccaat gaatgggggc actgacatgt actcttaaca tgtagtgcaa tccagagatc  600
ggatatccag acactggcag cacgatcgcc tcgcgccgta gatcacgcac gcaaattact  660
gaagaccatt cacaaaaaaa aaaaaacaca caggggctag cgtgccccac accaaaccca  720
agtgctgcgt tgcacgcagg ggagcgaaaa aaaacaataa tgctcactgt cacgtcgcgt  780
atccaacccc gcggacgtct cggctctcag cagcagcaca cggggcacct cacgatgccg  840
ttctcgttgc actccgtgca ccgccggaac ccgccgccgc attcgtcgcc ctcctcctcc  900
tcctccgcct cgtcttcgtc acccacgtac accttgcagc tgcccgagca gacatcgcag  960
agcacgaacc gcatgtcccc gcaggcctcg cacgcgccgg cgtcgccgcc gtgtgggccg  1020
gccgtcgacg cagcgctctc gcacccggcc agcctcggcg cgagctcccc ggcctcgtgc  1080
agccgcttca gctcctcggc gttgcccacg agctccccgt ccacgaagag gctggggagg  1140
gcggcgggcg tgccgccggc ttggccgagc ccgaggccga gaaggccgcg gagctcgtcc  1200
cggaacccgc ggtgcatgga cacgtcgcgc tcgtcgaggc gcacgccgta gcccttgagg  1260
atggcgcgcg ccaggcagca gtcctcgtgc gtggcgcgca cgccgcgcag cgacgtgaag  1320
tagagcaccg ccctccgcgg cggcagcgcc ttcccctccc cgccgctcgt cggggcggcg  1380
tcgggccgag gcatcggcat cggcagcggc gtcaccttgg cggacgccgc gaggtcctgc  1440
gcaggcgccg tggcgaccgg gaacgagaag gagtggcgcc cgaacggcgc gcccagcagc  1500
ggggagcggt cctcgaggcc ggccatgagc gcccacgcgt cgatgtcctc gggctcgttg  1560
ggcggcgtca tggtgggcgt gcgcggcgcc agcctcgtgg gcgcgggctc cggcgcccgc  1620
ggcagggcct tgtccagctc cagggacccg agcgtggacg acgtgagccg caccacgtgg  1680
acgccgacgt cgctggggca ccgagccggg aacgactggc tgcgcggcag cggtgacggg  1740
cagtaccgga ggtcgtgacg ggcctgcctt gaggtggtgc accccatggc accaatgtac  1800
acacacggcc aaagcgccaa gtgggctgca gactgcctgc caatgtgatc aagcagccag  1860
gagcagagac ggatctctgg ggatcggggt ttctggggtt taggatcttt atactactct  1920
gtcattgggg atataaaact aggagtgtgg ttaattagga ctcgatagat aagtttacca  1980
caagcgcgtg aaatggtcta cccgatgatg tgattggcct aaaaagaaca agaagagtat  2040
ttggagctac tgaacattct cttttcctga agataactaa tttttggaac attcagactt  2100
gggagtctgg actttggag ggaagttcaa attgtggtct gcctctgcca tgtgttgttt  2160
tttagtcgga gagtggccct catttttttt gtcctgttta gctttatagt cgtagcagct  2220
agtagcgaaa tttaaccttg gattatggcc gtgttagtca aacaatcatt gatttatttc  2280
ctccctttcg cgctgctttt cctgtacgca tctccgctgc ccttgattcg aggaccctgt  2340
tcacaacaca gggctctggc tttggagcct ctcgtttgta gcacttgcac gtagttaccc  2400
ggaccgaagc ttcaacacag atctgatagt ttaaacgctc ttcaactgga agagcggtta  2460
cccggaccga agcttcggcc ggggcccatc gatatccgcg ggcatgcctg cagtgcagcg  2520
tgacccggtc gtgcccctct ctagagataa tgagcattgc atgtctaagt tataaaaaat  2580
taccacatat ttttttgtc acacttgttt gaagtgcagt ttatctatct ttatacatat  2640
atttaaactt tactctacga ataatataat ctatagtact acaataatat cagtgtttta  2700
gagaatcata taaatgaaca gttagacatg gtctaaagga caattgagta ttttgacaac  2760
aggactctac agttttatct ttttagtgtg catgtgttct cctttttttt tgcaaatagc  2820
ttcacctata taatacttca tccattttat tagtacatcc atttagggtt tagggttaat  2880
ggtttttata gactaatttt tttagtacat ctattttatt ctattttagc ctctaaatta  2940
agaaaactaa aactctattt tagttttttt atttaataat ttagatataa aatagaataa  3000
aataaagtga ctaaaaatta aacaaatacc ctttaagaaa ttaaaaaaac taaggaaaca  3060
tttttcttgt ttcgagtaga taatgccagc ctgttaaacg ccgtcgacga gtctaacgga  3120
caccaaccag cgaaccagca gcgtcgcgtc gggccaagcg aagcagacgg cacggcatct  3180
```

```
ctgtcgctgc ctctggaccc ctctcgagag ttccgctcca ccgttggact tgctccgctg  3240
tcggcatcca gaaattgcgt ggcggagcgg cagacgtgag ccggcacggc aggcggcctc  3300
ctcctcctct cacggcaccg gcagctacgg gggattcctt tcccaccgct ccttcgcttt  3360
cccttcctcg cccgccgtaa taaatagaca cccccctccac accctctttc cccaacctcg  3420
tgttgttcgg agcgcacaca cacacaacca gatctccccc aaatccaccc gtcggcacct  3480
ccgcttcaag gtacgccgct cgtcctcccc ccccccccct ctctaccttc tctagatcgg  3540
cgttccggtc catggttagg gcccggtagt tctacttctg ttcatgtttg tgttagatcc  3600
gtgtttgtgt tagatccgtg ctgctagcgt tcgtacacgg atgcgacctg tacgtcagac  3660
acgttctgat tgctaacttg ccagtgtttc tctttgggga atcctgggat ggctctagcc  3720
gttccgcaga cgggatcgat ttcatgattt tttttgtttc gttgcatagg gtttggtttg  3780
ccccttttcct ttatttcaat atatgccgtg cacttgtttg tcgggtcatc ttttcatgct  3840
ttttttttgtc ttggttgtga tgatgtggtc tggttgggcg gtcgttctag atcggagtag  3900
aattctgttt caaactacct ggtggattta ttaattttgg atctgtatgt gtgtgccata  3960
catattcata gttacgaatt gaagatgatg gatggaaata tcgatctagg ataggtatac  4020
atgttgatgc gggttttact gatgcatata cagagatgct tttgttcgc ttggttgtga  4080
tgatgtggtg tggttgggcg gtcgttcatt cgttctagat cggagtagaa tactgtttca  4140
aactacctgg tgtatttatt aattttggaa ctgtatgtgt gtgtcataca tcttcatagt  4200
tacgagttta agatggatgg aaatatcgat ctaggatagg tatacatgtt gatgtgggtt  4260
ttactgatgc atatacatga tggcatatgc agcatctatt catatgctct aaccttgagt  4320
acctatctat tataataaac aagtatgttt tataattatt ttgatcttga tatacttgga  4380
tgatggcata tgcagcagct atatgtggat tttttttagcc ctgccttcat acgctattta  4440
tttgcttggt actgtttctt ttgtcgatgc tcaccctgtt gtttggtgtt acttctgcag  4500
gtcgactcta gaggatccaa caatggagaa caacatacag aatcagtgcg tcccctacaa  4560
ctgcctcaac aatcctgaag tagagattct caacgaagag aggtcgactg gcagattgcc  4620
gttagacatc tccctgtccc ttacacgttt cctgttgtct gagtttgttc caggtgtggg  4680
agttgcgttt ggcctcttcg acctcatctg ggcttcatc actccatctg attggagcct  4740
ctttcttctc cagattgaac agttgattga acaaaggatt gagaccttgg aaaggaatcg  4800
ggccatcact accccttcgtg gcttagcaga cagctatgag atctacattg aagcactaag  4860
agagtgggaa gccaatccta acaatgccca actgagagaa gatgtgcgta tacgctttgc  4920
taacacagat gatgctttga tcacagccat caacaacttc acccttacca gcttcgagat  4980
ccctcttctc tcggtctatg ttcaagctgc taacctgcac ttgtcactac tgcgcgacgc  5040
tgtgtcgttt gggcaaggtt ggggactgga catagctact gtcaacaatc actacaacag  5100
actcatcaat ctgattcatc gatacacgaa acattgtttg gatacctaca atcagggatt  5160
ggagaacctg agaggtacta acactcgcca atgggccagg ttcaatcagt tcaggagaga  5220
ccttacactt actgtgttag acatagttgc tctctttccg aactacgatg ttcgtaccta  5280
tccgattcaa acgtcatccc aacttacaag ggagatctac accagttcag tcattgaaga  5340
ctctccagtt tctgcgaaca tacccaatgg tttcaacagg gctgagtttg gagtcagacc  5400
accccatctc atggacttca tgaactcttt gtttgtgact gcagagactg ttagatccca  5460
aactgtgtgg ggaggacact tagttagctc acgcaacacg gctggcaatc gtatcaactt  5520
tcctagttac ggggtcttca atcccggggg cgccatctgg attgcagatg aagatccacg  5580
tcctttctat cggaccttgt cagatcctgt cttcgtccga ggaggctttg gcaatcctca  5640
ctatgtactc ggtcttaggg gagtggcctt tcaacaaact ggtacgaatc acacccgcac  5700
attcaggaac tccgggacca ttgactctct agatgagata ccacctcaag acaacagcgg  5760
cgcaccttgg aatgactact cccatgtgct gaatcatgtt acctttgtgc gctggccagg  5820
tgagatctca ggttccgact catggagagc accaatgttc tcttggacgc atcgtagcgc  5880
taccccccaca aacaccattg atccagagag aatcactcag attcccttgg tgaaggcaca  5940
cacacttcag tcaggaacta cagttgtaag agggccgggg ttcacgggag gagacattct  6000
tcgacgcact agtggaggac cattcgcgta caccattgtc aacatcaatg ggcaacttcc  6060
ccaaaggtat cgtgccagga tacgctatgc ctctactacc aatctaagaa tctacgttac  6120
ggttgcaggt gaacggatct ttgctggtca gttcaacaag acaatggata ccggtgatcc  6180
acttacattc caatctttct cctacgccac tatcaacacc gcgttcacct ttccaatgag  6240
ccagagcagt ttcacagtag gtgctgatac cttcagttca ggcaacgaag tgtacattga  6300
caggtttgag ttgattccag ttactgccac actcgagtaa ggatccgtcg acctgcagcc  6360
aagctttcgc gagctcgaga tccccgacat atgccccggt ttcgttgcga ctaacatgag  6420
ttcttggaca aatttgattg gacctgatga gatgatccaa cccgaggata tagcaaagct  6480
cgttcgtgca gcaatggaac ggccaaaccg tgcttttgtc cccaagaatg aggtgctatg  6540
catgaaggaa tctacccgtt gatgtccaac agtctcaggg ttaatgtcta tgtatcttaa  6600
ataatgttgt cggtattttg taatctcata tagattttca ctgtgcgacg caaaaatatt  6660
aaataaatat tattattatc tacgttttga ttgagatatc atcaatatta taataaaaat  6720
atccattaaa cacgatttga tacaaatgac agtcaataat ctgatttgaa tatttattaa  6780
ttgtaacgaa ttacataaag atcgaataga aaatactgca ctgcaaatga aaattaacac  6840
atactaataa atgcgtcaaa tatctttgcc aagatcaagc ggagtgaggg cctcatatcc  6900
ggtctcagtt acaagcacgg tatccccgaa gcgcgctcca ccaatgccct cgacatagat  6960
gccgggctcg acgctgagga cattgcctac cttgagcatg gtctcagcgc cggctttaag  7020
ctcaatccca tcccaatctg aatatcctat cccgcgccca gtccggtgta agaacgggtc  7080
tgtccatcca cctctgttgg gaattccggt ccgggtcacc tttgtccacc aagatggaac  7140
tgcggccagc ttgcatgcct gcagtgcagc gtgacccggt cgtgcccctc tctagagata  7200
atgagcattg catgtctaag ttataaaaaa ttaccacata tttttttttgt cacacttgtt  7260
tgaagtgcag tttatctatc tttatacata tatttaaact ttactctacg aataatataa  7320
tctatagtac tacaataata tcagtgtttt agagaatcat ataaatgaac agttagacat  7380
ggtctaaagg acaattgagt attttgacaa caggactcta cagttttatc tttttagtgt  7440
gcatgtgttc tcctttttttt ttgcaaatag cttcacctat ataatacttc atccatttta  7500
ttagtacatc catttagggt ttagggttaa tggtttttat agactaattt ttttagtaca  7560
tctattttat tctattttag cctctaaatt aagaaaacta aaactctatt ttagtttttt  7620
tatttaataa tttagatata aaatagaata aaataaagtg actaaaaatt aaacaaatac  7680
cctttaagaa attaaaaaaa ctaaggaaac atttttcttg tttcgagtag ataatgccag  7740
cctgttaaac gccgtcgacg agtctaacgg acaccaacca gcgaaccagc agcgtcgcgt  7800
cgggccaagc gaagcagacg gcacggcatc tctgtcgctg cctctggacc cctctcgaga  7860
gttccgctcc accgttggac ttgctccgct gtcggcatcc agaaattgcg tggcggagcg  7920
```

-continued

```
gcagacgtga gccggcacgg caggcggcct cctcctcctc tcacggcacc ggcagctacg  7980
ggggattcct ttcccaccgc tccttcgctt tcccttcctc gcccgccgta ataaatagac  8040
accccctcca caccctcttt ccccaacctc gtgttgttcg gagcgcacac acacacaacc  8100
agatctcccc caaatccacc cgtcggcacc tccgcttcaa ggtacgccgc tcgtcctccc  8160
cccccccccc tctctacctt ctctagatcg gcgttccggt ccatggttag ggcccggtag  8220
ttctacttct gttcatgttt gtgttagatc cgtgtttgtg ttagatccgt gctgctagcg  8280
ttcgtacacg gatgcgacct gtacgtcaga cacgttctga ttgctaactt gccagtgttt  8340
ctctttgggg aatcctggga tggctctagc cgttccgcag acgggatcga tttcatgatt  8400
tttttgttt cgttgcatag ggtttggttt gccctttttc tttatttcaa tatatgccgt  8460
gcacttgttt gtcgggtcat cttttcatgc ttttttttgt cttggttgtg atgatgtggt  8520
ctggttgggc ggtcgttcta gatcggagta gaattctgtt tcaaactacc tggtggattt  8580
attaattttg gatctgtatg tgtgtgccat acatattcat agttacgaat tgaagatgat  8640
ggatggaaat atcgatctag gataggtata catgttgatg cgggttttac tgatgcatat  8700
acagagatgc tttttgttcg cttggttgtg atgatgtggt gtggttgggc ggtcgttcat  8760
tcgttctaga tcggagtaga atactgtttc aaactacctg gtgtatttat taattttgga  8820
actgtatgtg tgtgtcatac atcttcatag ttacgagttt aagatggatg gaaatatcga  8880
tctaggatag gtatacatgt tgatgtgggt tttactgatg catatacatg atggcatatg  8940
cagcatctat tcatatgctc taaccttgag tacctatcta ttataataaa caagtatgtt  9000
ttataattat tttgatcttg atatacttgg atgatggcat atgcagcagc tatatgtgga  9060
tttttttagc cctgccttca tacgctattt atttgcttgg tactgtttct tttgtcgatg  9120
ctcaccctgt tgtttggtgt tacttctgca ggtcgactct agaggatcca cacgacacca  9180
tgtccgcccg cgaggtgcac atcgacgtga acaacaagac cggccacacc ctccagctgg  9240
aggacaagac caagctcgac ggcggcaggt ggcgcacctc cccgaccaac gtggccaacg  9300
accagatcaa gaccttcgtg gccgaatcca acggcttcat gaccggcacc gagggcacca  9360
tctactactc aattaatggc gaggccgaga tcagcctcta cttcgacaac ccgttcgccg  9420
gctccaacaa atacgacggc cactccaaca agtcccagta cgagatcatc acccagggcg  9480
gctccggcaa ccagtcccac gtgacctaca ccatccagac cacctcctcc cgctacggcc  9540
acaagtcctg agtcatgagt catgagtcag ttaacctaga cttgtccatc ttctggattg  9600
gccaacttaa ttaatgtatg aaataaaagg atgcacacat agtgacatgc taatcactat  9660
aatgtgggca tcaaagttgt gtgttatgtg taattactag ttatctgaat aaaagagaaa  9720
gagatcatcc atatttctta tcctaaatga atgtcacgtg tctttataat tctttgatga  9780
accagatgca tttcattaac caaatccata tacatataaa tattaatcat atataattaa  9840
tatcaattgg gttagcaaaa caaatctagt ctaggtgtgt tttgcgaatg cggccgcgga  9900
ccgaattggg gatctgcatg aaagaaactg tcgcactgct gaaccgcacc ttgtcacttt  9960
catcgaacac gacctgtgcc caagatgacg gtgctgcggt ctaagtgagg ctgaattgcc  10020
ttggacagaa gcggactccc tacaattagt taggccaaac ggtgcatcca tgtgtagctc  10080
cgggctcggg ctgtatcgcc atctgcaata gcatccatgg agctcgttcc atgtagttgg  10140
agatgaacca atgatcgggc gtgtggacgt atgttcctgt gtactccgat agtagagtac  10200
gtgttagctc tttcatggtg caagtgaaat ttgtgttggt ttaattaccc ctacgttagt  10260
tgcgggacag gagacacatc atgaatttaa aggcgatgat gtcctctcct gtaatgttat  10320
tcttttgatg tgatgaatca aaatgtcata taaaacattt gttgctcttt agttaggcct  10380
gatcgtagaa cgaaatgctc gtgtagcggg gctacgagcc tatgacgcaa taacactggt  10440
ttgccggccc ggagtcgctt gacaaaaaaa agcatgttaa gtttatttac aattcaaaac  10500
ctaacatatt atattccctc aaagcaggtt cacgatcaca cctgtaccta aaaaaaacat  10560
gaagaatata ttactccatt attatgagat gaaccacttg gcaagagtgg taagctatat  10620
aaaaaaatga acattattac gagatgttat atgccattat attgattcga agatatatgt  10680
ttctttctcc cacgggcacc taacggatac atgataaggc caaggcagat cacgggaaat  10740
tattcgaata catgttacgc cctattgccg gaaaaaaaat gcagggcagg tgttggccgt  10800
agcgatttaa gcacttaagc tggaggttgc cacacttgga tgcaagcgtc tgacccttct  10860
aaaaaatcgg cggctttgtc cgtatccgta tcccctatcc aacatctagc tggccacacg  10920
acggggctgg gcagatcgtg gatgccgggt cgacgtcgat cgtcagccat catagaccaa  10980
tcgaccatct gttatggatg cttgctagct agactagtca gacataaaat ttggatactt  11040
tctcccaact gggagacggg gactgatgtg cagctgcacg tgagctaaat ttttccctat  11100
aaatatgcat gaaatactgc attatcttgc cacagccact gccacagcca gataacaagt  11160
gcagctggta gcacgcaacg catagctctg gacttgtagc taggtagcca accggatcca  11220
cacgacacca tgctcgacac caacaaggtg tacgagatca gcaaccacgc caacggcctc  11280
tacgccgcca cctacctctc cctcgacgac tccggcgtgt ccctcatgaa caagaacgac  11340
gacgacatcg acgactacaa cctcaagtgg ttcctcttcc cgatcgacga cgaccagtac  11400
atcatcacct cctacgccgc caacaactgc aaggtgtgga acgtgaacaa cgacaagatt  11460
aatgtgtcaa cctactcctc caccaactcc atccagaagt ggcagatcaa ggccaacggc  11520
tcctcctacg tgatccagtc cgacaacggc aaggtgctca ccgccggcac cggccaggcc  11580
ctcggcctca tccgcctcac cgacgagtcc tccaacaacc cgaaccagca atggaacctg  11640
acgtccgtgc agaccatcca gctcccgcag aagccgatca tcgacaccaa gctcaaggac  11700
tacccgaagt actccccgac cggcaacatc gacaacggca cctccccgca gctcatgggc  11760
tggaccctcg tgccgtgcat catggtgaac gacccgaaca tcgacaagaa cacccagatc  11820
aagaccaccc cgtactacat cctcaagaag taccagtact ggcagagggc cgtgggctcc  11880
aacgtcgcgc tccgcccgca cgagaagaag tcctacacct acgagtgggg caccgagatc  11940
gaccagaaga ccaccatcat caacaccctc ggcttccaga tcaacatcga cagcggcatg  12000
aagttcgaca tcccggaggt gggcggcggt accgacgaga tcaagaccca gctcaacgag  12060
gagctcaaga tcgagtattc acatgagacg aagatcatgg agaagtacca ggagcagtcc  12120
gagatcgaca acccgaccga ccagtccatg aactccatcg gcttcctcac catcacctcc  12180
ctggagctct accgctacaa cggctccgag atccgcatca tgcagatcca gacctccgac  12240
aacgacacct acaacgtgac ctcctacccg aaccaccagc aggccctgct gctgctgacc  12300
aaccactcct acgaggaggt ggaggagatc accaacatcc cgaagtccac cctcaagaag  12360
ctcaagaagt actacttctg agtcatgagt catgagtcag ttaacctaga cttgtccatc  12420
ttctggattg gccaacttaa ttaatgtatg aaataaaagg atgcacacat agtgacatgc  12480
taatcactat aatgtgggca tcaaagttgt gtgttatgtg taattactag ttatctgaat  12540
aaaagagaaa gagatcatcc atatttctta tcctaaatga atgtcacgtg tctttataat  12600
tctttgatga accagatgca tttcattaac caaatccata tacatataaa tattaatcat  12660
```

```
atataattaa tatcaattgg gttagcaaaa caaatctagt ctaggtgtgt tttgcgaatt  12720
atcgatgggc cccggccgaa gctggccgcg gaccgaattc ccatggagtc aaagattcaa  12780
atagaggacc taacagaact cgccgtaaag actggcgaac agttcataca gagtctctta  12840
cgactcaatg acaagaagaa aatcttcgtc aacatggtgg agcacgacac gcttgtctac  12900
tccaaaaata tcaaagatac agtctcagaa gaccaaaggg caattgagac ttttcaacaa  12960
agggtaatat ccggaaacct cctcggattc cattgcccag ctatctgtca ctttattgtg  13020
aagatagtgg aaaaggaagg tggctcctac aaatgccatc attgcgataa aggaaaggcc  13080
atcgttgaag atgcctctgc cgacagtggt cccaaagatg gacccccacc cacgaggagc  13140
atcgtggaaa aagaagacgt tccaaccacg tcttcaaagc aagtggattg atgtgatatc  13200
tccactgacg taagggatga cgcacaatcc cactatcctt cgcaagaccc ttcctctata  13260
taaggaagtt catttcattt ggagaggaca gggtacccgg ggatccacca tgtctccgga  13320
gaggagacca gttgagatta ggccagctac agcagctgat atggccgcgg tttgtgatat  13380
cgttaaccat tacattgaga cgtctacagt gaactttagg acagagccac aaacaccaca  13440
agagtggatt gatgatctag agaggttgca agatagatac ccttggttgg ttgctgaggt  13500
tgagggtgtt gtggctggta ttgcttacgc tgggccctgg aaggctagga acgcttacga  13560
ttggacagtt gagagtactg tttacgtgtc acataggcat caaaggttgg gcctaggatc  13620
cacattgtac acacatttgc ttaagtctat ggaggcgcaa ggttttaagt ctgtggttgc  13680
tgttataggc cttccaaacg atccatctgt taggttgcat gaggctttgg gatacacagc  13740
ccggggtaca ttgcgcgcag ctggatacaa gcatggtgga tggcatgatg ttggtttttg  13800
gcaaagggat tttgagttgc cagctcctcc aaggccagtt aggccagtta cccagatctg  13860
agtcgacctg caggcatgcc cgctgaaatc accagtctct ctctacaaat ctatctctct  13920
ctataataat gtgtgagtag ttcccagata agggaattag ggttcttata gggtttcgct  13980
catgtgttga gcatataaga aacccttagt atgtatttgt atttgtaaaa tacttctatc  14040
aataaaattt ctaattccta aaaccaaaat ccagggcgag ctcgaattcg agctcgagcc  14100
cgggtggatc ctctagagtc gacctgcaga agcttcggtc cggcgcgcct ctagttgaag  14160
acacgttcat gtcttcatcg taagaagaca ctcagtagtc ttcggccaga atggcctaac  14220
tcaaggccat cgtggcctct tgctcttcag gatgaagagc tatgtttaaa cgtgcaagcg  14280
ctactagaca attcagtaca ttaaaaacgt ccgcaatgtg ttattaagtt gtctaagcgt  14340
caatttggaa caagtggcta tcgccagata taagaacttc gatccgaaat atcgtttcaa  14400
aactagaaaa cagcgcggct ttggctaagc cgcgcactat ataggatttt gggcaccttt  14460
tgatggaacg tgaaagcgta ctgcgcacta gttatttagg ttgaaccttg gatatacggt  14520
tctcactgcg ccaatgcaag gcttgaaact tggttagtaa tacgtactcc ctccgtttct  14580
ttttatttgt cgctggatag tgcaatttttg cactatcgag cgacaaataa aaagaaacgg  14640
agggagtata tgattgtcag atgtagatat gtttatttat atatcacata cagatatata  14700
aaacagatca ctttttcaga tatacagttc caatgtcagc cctgatcacc ctgtcataaa  14760
ttgcacgttt ctaattgatg ttgcttcatg gtcgtcatga gaaccttctg aagaaatcga  14820
tgaaggttgc caacctttca aagtttcaga aaccactttg catgtacact aagggctggt  14880
ttggcagccc aaaaccagcc agcgttttcc tggtcttttc tcccgggaga aagcccatgc  14940
atagattgtc cctggattat ttatctgtgt cctttggcta aaaattcgtc ccaatttcct  15000
gtaggaaact acctcggcct tgggaggcca ggcgattctc caccgcctcg tctcgtccat  15060
ccttcgatgc tcacgcgtgc ctcctcggat gctatcctca ggcgattctc cgtcgtctcg  15120
tctcatccat cctcacgcgc gcctcctccg acgctatccc caggcgattc tccaccgtct  15180
cgtctcatcc atcctcatgt acgcctcgtc cgatgctatc cccagacgat tttccgtcgt  15240
ctcatctcct tcatgctcgc gcgcgcctcc tccgacgcta tccccaggcg atttttctgc  15300
cgtctcgtct ccttcatgcc cgcgcgcgcc tcctccgacg ctatccccag gcgattttcc  15360
gccgtctcgt ctccttcatg cccgcgcgtg cctcctccga cgctattccc acgagcgcct  15420
ccgccgccgc tatccccaga cgattttccg ctgtctcgtc tccttcatgc ccgcgcgccc  15480
ctcctccgac gctatcccca cgagcgcctc cgccgccgct ccaccgtctt ccccgccgcc  15540
atccccttaa ttcctataga tctggacccc gctctacttt cgttggcata cttttgcttg  15600
gtgtgcgcgg gctggagtgg aaggttgcgc attcgatcac gggggagaag tggatcttgg  15660
gtcttggcag gctagggcgg ttgccaggac gccgtggtgt gcattcatgg gtcctataaa  15720
tctttatcat taccgcctta ggagctagtt gtagttcaca catcatatcc ttttctgctc  15780
gacatcgtct ggggatgccc taggtgccct accgacccta cggcattgtc ttgacctcta  15840
ttagactcta tgtcatctag agccttcttg ggtggccttt tgaccccaaa gcgaccctat  15900
gatcttaccc taacgaggtc tcccttggtg gggcaagatc cactttgtcc acttaactga  15960
agatctgatc ctcatcttga aatctttaat cccaaggtga ctctacgtcg tatgtggatg  16020
ctccgggtaa cctgccaacc cggatcaccc taagatctct ttcctaaggg gcgagatcta  16080
ggttcctacg agaaagaaga cgaccctgca ccattgcggt ccgtccggtc cagagtgcga  16140
acgtccggat gcgacacagg gaaggagtcg ctcctgcagc gaggtcgcag actgtccaca  16200
cagcctcaga aggcaccgcc agacaataca tgtaataccc actctgtaag aaaaacctaa  16260
aaggagaaag tatattcctt tatctatatg tgtgttatat ttctactcac catcacatgt  16320
gaacatctca cttacacaaa taaataatta acaaaagaca ctcaaataaa ttatgcatca  16380
tgctcgacct tattttgtgt gcattctgtt acaatataaa aataatataa aaaacatata  16440
ttaatatcaa aatttggaga tttaacccta atatgcaaat cggagtttag aggaaagaaa  16500
gaaaaatgct atacaaaata aaggaataaa tatataaata aaggtaaaac tattaatact  16560
ggtatattaa tttgaacagt tgacctaatt atgaatatca caactggttt gaattcaaat  16620
atgaaatcca agaatttgga aataggaaaa atggagataa gaataaagga aaagaattct  16680
taactcggat gggcctggga aacgaatttc ggcccacttc ctgtgtcctt agctgtgcgg  16740
ctcagtccag tg                                                       16752
```

```
SEQ ID NO: 7          moltype = DNA  length = 26
FEATURE               Location/Qualifiers
misc_feature          1..26
                      note = Primer 09-0-2877
source                1..26
                      mol_type = other DNA
                      organism = synthetic construct
SEQUENCE: 7
agggcctcat atccggtctc agttac                                        26
```

```
SEQ ID NO: 8            moltype = DNA  length = 29
FEATURE                 Location/Qualifiers
misc_feature            1..29
                        note = Primer 09-0-2880
source                  1..29
                        mol_type = other DNA
                        organism = synthetic construct
SEQUENCE: 8
cacgctgcac tgcaggcatg caagctggc                                   29

SEQ ID NO: 9            moltype = DNA  length = 25
FEATURE                 Location/Qualifiers
misc_feature            1..25
                        note = Primer 02-0-197
source                  1..25
                        mol_type = other DNA
                        organism = synthetic construct
SEQUENCE: 9
ccgctgtatc acaagggctg gtacc                                       25

SEQ ID NO: 10           moltype = DNA  length = 25
FEATURE                 Location/Qualifiers
misc_feature            1..25
                        note = Primer 02-0-198
source                  1..25
                        mol_type = other DNA
                        organism = synthetic construct
SEQUENCE: 10
ggagcccgtg tagagcatga cgatc                                       25

SEQ ID NO: 11           moltype = DNA  length = 29
FEATURE                 Location/Qualifiers
misc_feature            1..29
                        note = Primer 09-0-3030
source                  1..29
                        mol_type = other DNA
                        organism = synthetic construct
SEQUENCE: 11
gagcatatcc agcaccagct ggtaccaag                                   29

SEQ ID NO: 12           moltype = DNA  length = 19
FEATURE                 Location/Qualifiers
misc_feature            1..19
                        note = Primer 09-0-2787
source                  1..19
                        mol_type = other DNA
                        organism = synthetic construct
SEQUENCE: 12
gcaggcatgc ccgcggata                                              19

SEQ ID NO: 13           moltype = DNA  length = 26
FEATURE                 Location/Qualifiers
misc_feature            1..26
                        note = Primer 09-0-3036
source                  1..26
                        mol_type = other DNA
                        organism = synthetic construct
SEQUENCE: 13
tggtctaccc gatgatgtga ttggcc                                      26

SEQ ID NO: 14           moltype = DNA  length = 29
FEATURE                 Location/Qualifiers
misc_feature            1..29
                        note = Primer 09-0-3046
source                  1..29
                        mol_type = other DNA
                        organism = synthetic construct
SEQUENCE: 14
cgaagacagg atctgacaag gtccgatag                                   29

SEQ ID NO: 15           moltype = DNA  length = 35
FEATURE                 Location/Qualifiers
misc_feature            1..35
                        note = Primer 09-0-3045
source                  1..35
                        mol_type = other DNA
                        organism = synthetic construct
SEQUENCE: 15
```

```
gacttcatga actctttgtt tgtgactgca gagac                              35

SEQ ID NO: 16          moltype = DNA  length = 22
FEATURE                Location/Qualifiers
misc_feature           1..22
                       note = Primer 09-0-2980
source                 1..22
                       mol_type = other DNA
                       organism = synthetic construct
SEQUENCE: 16
ctcatgactc aggacttgtg gc                                            22

SEQ ID NO: 17          moltype = DNA  length = 18
FEATURE                Location/Qualifiers
misc_feature           1..18
                       note = Primer 08-0-2463
source                 1..18
                       mol_type = other DNA
                       organism = synthetic construct
SEQUENCE: 17
atcagcctct acttcgac                                                 18

SEQ ID NO: 18          moltype = DNA  length = 23
FEATURE                Location/Qualifiers
misc_feature           1..23
                       note = Primer 08-0-2759
source                 1..23
                       mol_type = other DNA
                       organism = synthetic construct
SEQUENCE: 18
ctccatgatc ttcgtctcat gtg                                           23

SEQ ID NO: 19          moltype = DNA  length = 23
FEATURE                Location/Qualifiers
misc_feature           1..23
                       note = Primer 09-0-2775
source                 1..23
                       mol_type = other DNA
                       organism = synthetic construct
SEQUENCE: 19
caccaactcc atccagaagt ggc                                           23

SEQ ID NO: 20          moltype = DNA  length = 26
FEATURE                Location/Qualifiers
misc_feature           1..26
                       note = Primer 09-0-3083
source                 1..26
                       mol_type = other DNA
                       organism = synthetic construct
SEQUENCE: 20
gccttgcatt ggcgcagtga gaaccg                                        26

SEQ ID NO: 21          moltype = DNA  length = 27
FEATURE                Location/Qualifiers
misc_feature           1..27
                       note = Primer 09-0-2799
source                 1..27
                       mol_type = other DNA
                       organism = synthetic construct
SEQUENCE: 21
cggcgcgcct ctagttgaag acacgtt                                       27

SEQ ID NO: 22          moltype = DNA  length = 30
FEATURE                Location/Qualifiers
misc_feature           1..30
                       note = Primer 09-0-3005
source                 1..30
                       mol_type = other DNA
                       organism = synthetic construct
SEQUENCE: 22
cactggactg agccgcacag ctaaggacac                                    30

SEQ ID NO: 23          moltype = DNA  length = 28
FEATURE                Location/Qualifiers
misc_feature           1..28
                       note = Primer 09-0-3230
source                 1..28
                       mol_type = other DNA
                       organism = synthetic construct
```

```
SEQUENCE: 23
ggaacattca gacttgggag tctggact                                28

SEQ ID NO: 24          moltype = DNA  length = 27
FEATURE                Location/Qualifiers
misc_feature           1..27
                       note = Primer 09-0-3229
source                 1..27
                       mol_type = other DNA
                       organism = synthetic construct
SEQUENCE: 24
gaacagggtc ctcgaatcaa gggcagc                                 27

SEQ ID NO: 25          moltype = DNA  length = 26
FEATURE                Location/Qualifiers
misc_feature           1..26
                       note = Primer 09-0-3231
source                 1..26
                       mol_type = other DNA
                       organism = synthetic construct
SEQUENCE: 25
cggttctcac tgcgccaatg caaggc                                  26

SEQ ID NO: 26          moltype = DNA  length = 23
FEATURE                Location/Qualifiers
misc_feature           1..23
                       note = Primer 09-0-3084
source                 1..23
                       mol_type = other DNA
                       organism = synthetic construct
SEQUENCE: 26
catgacgacc atgaagcaac atc                                     23

SEQ ID NO: 27          moltype = DNA  length = 20
FEATURE                Location/Qualifiers
misc_feature           1..20
                       note = 5' Junction Sequence
source                 1..20
                       mol_type = other DNA
                       organism = synthetic construct
SEQUENCE: 27
caacacagat ctgatagttt                                         20

SEQ ID NO: 28          moltype = DNA  length = 20
FEATURE                Location/Qualifiers
misc_feature           1..20
                       note = 3' Junction Sequence
source                 1..20
                       mol_type = other DNA
                       organism = synthetic construct
SEQUENCE: 28
cgtcaatttg gaacaagtgg                                         20

SEQ ID NO: 29          moltype = DNA  length = 23
FEATURE                Location/Qualifiers
misc_feature           1..23
                       note = Primer 08-O-2677
source                 1..23
                       mol_type = other DNA
                       organism = synthetic construct
SEQUENCE: 29
cgtttgtagc acttgcacgt agt                                     23

SEQ ID NO: 30          moltype = DNA  length = 22
FEATURE                Location/Qualifiers
misc_feature           1..22
                       note = Primer 08-O-2678
source                 1..22
                       mol_type = other DNA
                       organism = synthetic construct
SEQUENCE: 30
ggtaaccgct cttccagttg aa                                      22

SEQ ID NO: 31          moltype = DNA  length = 17
FEATURE                Location/Qualifiers
misc_feature           1..17
                       note = Probe 08-QP74
source                 1..17
                       mol_type = other DNA
```

-continued

```
                       organism = synthetic construct
SEQUENCE: 31
aagcttcaac acagatc                                                17

SEQ ID NO: 32          moltype = DNA  length = 90
FEATURE                Location/Qualifiers
misc_feature           1..90
                       note = Amplicon
source                 1..90
                       mol_type = other DNA
                       organism = synthetic construct
SEQUENCE: 32
cgtttgtagc acttgcacgt agttacccgg accgaagctt caacacagat ctgatagttt  60
aaacgctctt caactggaag agcggttacc                                  90

SEQ ID NO: 33          moltype = DNA  length = 24
FEATURE                Location/Qualifiers
misc_feature           1..24
                       note = Forward primer 11-O-4127
source                 1..24
                       mol_type = other DNA
                       organism = synthetic construct
SEQUENCE: 33
ggaccctgtt cacaacacag ggct                                        24

SEQ ID NO: 34          moltype = DNA  length = 19
FEATURE                Location/Qualifiers
misc_feature           1..19
                       note = Reverse primer 11-O-4128
source                 1..19
                       mol_type = other DNA
                       organism = synthetic construct
SEQUENCE: 34
ggccgaagct tcggtccgg                                              19

SEQ ID NO: 35          moltype = DNA  length = 149
FEATURE                Location/Qualifiers
misc_feature           1..149
                       note = Amplicon
source                 1..149
                       mol_type = other DNA
                       organism = synthetic construct
SEQUENCE: 35
ggaccctgtt cacaacacag ggctctggct ttggagcctc tcgtttgtag cacttgcacg  60
tagttacccg gaccgaagct tcaacacaga tctgatagtt taaacgctct tcaactggaa  120
gagcggttac ccggaccgaa gcttcggcc                                   149
```